US011458289B2

(12) United States Patent
Moeckly et al.

(10) Patent No.: US 11,458,289 B2
(45) Date of Patent: Oct. 4, 2022

(54) APPLICATOR FOR APPLYING A MICRONEEDLE ARRAY TO SKIN

(71) Applicant: KINDEVA DRUG DELIVERY L.P., Saint Paul, MN (US)

(72) Inventors: Craig S. Moeckly, White Bear Lake, MN (US); Michael J. Frits, Lake Elmo, MN (US); Steven P. Gowers, Cambridge (GB); Gregory R. Ley, Blaine, MN (US); Richard R. Mathias, Brookline, MA (US); Robert G. M. Selby, Hertfordshire (GB); Ryan Patrick Simmers, Fargo, MN (US); Michael B. Sivigny, Lake Elmo, MN (US); Daniel G. T. Strange, Cambridge (GB)

(73) Assignee: Kindeva Drug Delivery L.P., Woodbury, MN (US)

( * ) Notice: Subject to any disclaimer, the term of this patent is extended or adjusted under 35 U.S.C. 154(b) by 84 days.

(21) Appl. No.: 16/754,881

(22) PCT Filed: Oct. 17, 2018

(86) PCT No.: PCT/IB2018/058049
§ 371 (c)(1),
(2) Date: Apr. 9, 2020

(87) PCT Pub. No.: WO2019/077519
PCT Pub. Date: Apr. 25, 2019

(65) Prior Publication Data
US 2020/0289808 A1 Sep. 17, 2020

Related U.S. Application Data

(60) Provisional application No. 62/589,717, filed on Nov. 22, 2017, provisional application No. 62/573,513, filed on Oct. 17, 2017.

(51) Int. Cl.
*A61M 37/00* (2006.01)

(52) U.S. Cl.
CPC . *A61M 37/0015* (2013.01); *A61M 2037/0023* (2013.01); *A61M 2205/584* (2013.01); *A61M 2210/04* (2013.01)

(58) Field of Classification Search
CPC ...... A61M 37/0015; A61M 2037/0023; A61M 2205/584; A61M 2210/04; A61M 35/00;
(Continued)

(56) References Cited

U.S. PATENT DOCUMENTS 6,091,975 A 7/2000 Daddona et al.
6,312,612 B1 11/2001 Sherman et al.
(Continued)

FOREIGN PATENT DOCUMENTS

CN 2418890 Y 2/2001
JP 6069287 2/2015
(Continued)

OTHER PUBLICATIONS

First Chinese Office Action for CN 201880067029.8 issued by the Chinese Patent Office dated Jun. 3, 2021; 15 pgs. including English Translation.
(Continued)

*Primary Examiner* — Amber R Stiles
(74) *Attorney, Agent, or Firm* — Mueting Raasch Group

(57) ABSTRACT

An applicator and method for applying a microneedle array to skin. The applicator can include a body having a first portion and a second portion defining a cavity, the second portion having a slot presented on an outside surface for insertion of the microneedle array into the cavity. The first portion and the second portion are slidable relative to one other along an axis enabling the body to be in an unprimed configuration and a primed configuration. The applicator
(Continued)

further includes a door operable with the second portion, the door being movable from a first door position to a second door position, wherein when the device is in the unprimed configuration, the door at least partially obstructs the slot and access into the cavity. When the device is in the primed configuration, the door does not obstruct the slots and enables access into the cavity.

9 Claims, 20 Drawing Sheets

(58) Field of Classification Search
CPC ................ A61M 37/00; A61M 35/003; A61M 37/0069; A61M 2037/0061; A61M 2205/8281
See application file for complete search history.

(56) References Cited

U.S. PATENT DOCUMENTS

| | | |
|---|---|---|
| 6,379,324 B1 | 4/2002 | Gartstein et al. |
| 6,558,361 B1 | 5/2003 | Yeshurun |
| 7,648,484 B2 | 6/2010 | Yeshurun et al. |
| 8,003,122 B2 | 8/2011 | Zhao |
| 10,300,260 B2 | 5/2019 | Wirtanen et al. |
| 10,828,480 B2 | 11/2020 | Nishimura et al. |
| 2004/0049150 A1 | 3/2004 | Dalton et al. |
| 2005/0148926 A1 | 7/2005 | Trautman et al. |
| 2005/0261631 A1 | 11/2005 | Clarke et al. |
| 2006/0217663 A1 | 9/2006 | Douglas |
| 2008/0039805 A1 | 2/2008 | Frederickson et al. |
| 2011/0213335 A1 | 9/2011 | Burton et al. |
| 2012/0123387 A1 | 5/2012 | Gonzalez et al. |
| 2012/0184906 A1 | 7/2012 | McAllister |
| 2014/0343502 A1 | 11/2014 | Constantineau et al. |
| 2016/0235958 A1* | 8/2016 | Quan ................ A61M 37/0015 |
| 2017/0224921 A1 | 8/2017 | Takabatake et al. |

FOREIGN PATENT DOCUMENTS

| | | |
|---|---|---|
| WO | WO 99/33504 A1 | 7/1999 |
| WO | WO 2002/30281 A1 | 4/2002 |
| WO | WO 2002/30300 A2 | 4/2002 |
| WO | WO 2002/30301 A1 | 4/2002 |
| WO | WO 2005/44333 A2 | 5/2005 |
| WO | 2010052692 | 5/2010 |
| WO | WO 2012/074576 A1 | 6/2012 |
| WO | WO 2012/122162 A1 | 9/2012 |
| WO | 2014110016 | 7/2014 |
| WO | 2014153447 | 9/2014 |
| WO | 2017038499 | 3/2017 |

OTHER PUBLICATIONS

Extended EP Search Report for EP 18867827.0 issued by the European Patent Office dated Aug. 10, 2021; 12 pgs.

* cited by examiner

APPLICATOR FOR APPLYING A MICRONEEDLE ARRAY TO SKIN

CROSS REFERENCE TO RELATED APPLICATIONS

This application is a national stage filing under 35 U.S.C. 371 of PCT/IB2018/058049, filed Oct. 17, 2018, which claims the benefit of U.S. Provisional Application No. 62/573,513, filed Oct. 17, 2017 and U.S. Provisional Application No. 62/589,717, filed Nov. 22, 2017, the disclosures of which are incorporated by reference in their entirety herein.

FIELD

The present disclosure generally relates to applicators and methods for applying a microneedle device to skin to treat an area of the skin and/or to deliver an active agent to a patient.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which includes the majority of epidermal cells, that lose their nuclei and become corneocytes. These dead cells make up the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or combinations of these treatment methods.

Devices including arrays of relatively small structures, sometimes referred to as microneedles or micro-pins, have been disclosed for use in connection with the delivery of therapeutic agents and other substances through the skin and other surfaces. The devices can be pressed against the skin in an effort to pierce the stratum corneum, such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays and patches can be deployed with an applicator capable of being used a number of different times. The microneedle arrays and patches are generally used once and then discarded. The applicator devices can be repeatedly reloaded with new microneedle arrays and patches. The present disclosure describes a microneedle array applicator device.

SUMMARY

The present disclosure relates to applicators that can be used to treat a selected site (e.g., on skin), and/or to apply an active ingredient to the treated site. Various embodiments include, but are not are not limited to, the following:

1. A device for applying a microneedle array to a surface, said device comprising:
   a body comprising a first portion and a second portion defining a cavity, said second portion comprising a slot presented on an outside surface of said second portion for insertion of the microneedle array into said cavity, said first portion and said second portion slidable relative to one other along an axis enabling said body to be in an unprimed configuration and a primed configuration; and
   a door operable with said second portion, said door being movable from a first door position to a second door position,
      wherein when said device is in the unprimed configuration, said door is in said first door position and at least partially obstructing said slot and access into said cavity, and
      wherein when said device is in said primed configuration, said door is in said second door position and not obstructing said slot to enable access into said cavity.

2. The device of embodiment 1, further comprising a microneedle array.

3. The device of embodiment 2, wherein said microneedle array comprises a plurality of microneedles.

4. The device of embodiment 1, further comprising coloring or other visual indicia proximate said slot identifying a location of said slot to a user.

5. The device of embodiment 1, further comprising presenting coloring or other visual indicia on said door, such that when said door is in said first door position, a user knows that said door is at least partially obstructing access into said cavity.

6. The device of embodiment 1, further comprising a biasing member for biasing said door to said first position when in said unprimed configuration.

7. The device of embodiment 5, wherein said biasing member comprises a compression spring.

8. The device of embodiment 1, further comprising a plunger disposed in said cavity, said plunger comprising a first plunger end and a second plunger end, said plunger movable from a first plunger position when said device is in said unprimed configuration to a second plunger position when said device is in said primed configuration, wherein said second plunger end operably engages with said door to move said door to said second door position when said plunger moves to said second plunger position.

9. The device of embodiment 8, further comprising a biasing member for biasing said plunger to said first plunger position when said body is in said unprimed configuration.

10. The device of embodiment 9, wherein said biasing member comprises a compression spring.

11. The device of embodiment 10, wherein said compression spring is compressed and energized when said plunger is in said second plunger position when said body is in said primed configuration.

12. A device for applying a microneedle array to a surface, said device comprising:
a body comprising a first portion and a second portion defining a cavity, said second portion comprising a slot presented on an outside surface of said second portion for insertion of the microneedle array into said cavity, said first portion and said second portion slidable relative to one other along an axis thus enabling said body to be in an unprimed configuration and a primed configuration; and
a plunger disposed in said cavity, said plunger comprising a first plunger end and a second plunger end, said plunger movable from a first position when said device is in said unprimed configuration to a second position when said device is in said primed configuration,
wherein when said device is in said primed configuration, a microneedle array can be inserted into said cavity through said slot and positioned such that it is proximate said second plunger end.

13. The device of embodiment 12, further comprising a microneedle array.

14. The device of embodiment 12, wherein a microneedle array is inserted in said slot and positioned proximate said second plunger end, the microneedle array and said second plunger end are in contact with one another.

15. The device of embodiment 12, wherein a microneedle array is inserted in said slot and positioned proximate said second plunger end, the microneedle array and said second plunger end are less than about 2 mm from one another.

16. The device of embodiment 12, wherein a microneedle array is inserted in said slot and positioned proximate said second plunger end, the microneedle array and said second plunger end are less than about 1 mm from one another.

17. The device of embodiment 12, wherein a microneedle array is inserted in said slot and positioned proximate said second plunger end, the microneedle array and said second plunger end are less than about 0.5 mm from one another.

18. The device of embodiment 12, wherein said second portion comprises an inner surface comprising a low surface energy material, wherein when said plunger moves from said first position to said second position, any friction between microneedle array and said inner surface, should they be in slidable engagement with one another, is minimized.

19. The device of embodiment 12, further comprising a biasing member for biasing said plunger to said first plunger position when said body is in said unprimed configuration.

20. The device of embodiment 19, wherein said biasing member comprises a compression spring.

21. The device of embodiment 20, wherein said compression spring is compressed and energized when said plunger is in said second plunger position when said body is in said primed configuration.

22. An insert for use with a microneedle array applicator including a housing defining a cavity and a delivery mechanism presented in the housing movable between a first position and a second position, said insert comprising:
a first end for insertion into the cavity of the applicator and a second end generally opposed said first end; and
a border structure extending from said first end to said second end, said border structure comprising an inner surface and an outer surface, said inner surface defining an opening comprising one or more projections extending from said inner surface into said opening,
wherein said border structure substantially, but not completely, encloses said opening, such that there is a gap in said border structure proximate said first end.

23. An insert for use with device for applying a microneedle array including a housing defining a cavity and a delivery mechanism presented in the housing movable between a first position and a second position, said insert comprising:
a first end for insertion into the cavity of the applicator and a second end generally opposed said first end; and
a border structure extending from said first end to said second end, said border structure comprising an inner surface and an outer surface, said inner surface defining an opening comprising one or more projections extending from said inner surface into said opening,
wherein said one or more projections are comprised of a low surface energy material.

24. The insert of embodiment 23, wherein the microneedle array includes an adhesive on portion thereof, said adhesive adhering to said one or more projections comprising said low surface energy material.

25. A method of applying a microneedle array to skin, the method comprising: providing a device for applying comprising:
a body comprising a longitudinal axis and a first portion and a second portion defining a cavity, said second portion comprising a slot presented on an outside surface of said second portion for insertion of a microneedle array into said cavity, said first portion and said second portion slidable relative to one other along said longitudinal axis to enable said body to be in an unprimed configuration and a primed configuration;
a door operable with said second portion, said door being movable from a first door position to a second door position,
wherein when said device is in the unprimed configuration, said door is in said first door position and at least partially obstructing said slot and access into said cavity, and
wherein when said device is in said primed configuration, said door is in said second door position and not obstructing said slot to enable access into said cavity; and
a plunger comprising a first end and a second end and disposed in said cavity, said plunger movable from a first plunger position when said device is in said unprimed configuration to a second plunger position when said device is in said primed configuration, said plunger further comprising a post comprising a post width,
wherein when said device is in said primed configuration, a microneedle array can be inserted into said cavity through said slot and positioned such that it is proximate said second end of said plunger, and
wherein when said device is in said primed configuration, a plunger spring associated with said plunger is compressed and energized;
axially compressing said first portion and said second portion of such that said first portion and said second portion operably are slidably moving relative to one other along an axis enabling device to be moved from said unprimed configuration to said primed configuration;
inserting said microneedle array into said cavity through said slot, such that said microneedle array is positioned proximate said second end of said plunger;
axially compressing said first portion and said second portion causing releasing said plunger, wherein said plunger spring when energized drives said microneedle array towards a patient's skin such that it is delivered to the patient's skin.

26. The method of embodiment 25, further comprising:
providing an insert comprising a border structure extending from said first end to said second end, said border structure comprising an inner surface and an outer surface, said inner surface defining an opening comprising one or more projections extending from said inner surface into said opening, wherein the microneedle array includes an adhesive on portion thereof, said adhesive adhering to said one or more projections comprising said low surface energy material such that the microneedle array is positioned in opening,
wherein said border structure substantially, but not completely, encloses said opening, such that there is a gap in said border structure proximate said first end, said gap being about the same size as said post width or larger,
wherein said step of inserting said microneedle array into said cavity through said slot comprises inserting said insert into said cavity through said slot; and
removing said insert from said cavity after said microneedle array has been to the patient's skin, wherein during such removal, said gap moves past said plunger post enabling insert to be removed when plunger is in said first plunger position.

27. A kit for applying a microneedle array to skin comprising providing a device of any of embodiments 1-24 and instructions for the method of any of embodiments 25-26.

In embodiments wherein low surface energy materials are used, such material can preferably comprise a surface energy of less than about 37 mJ/mm$^2$, less than about 29 mJ/mm$^2$, or less than about 18 mJ/mJ/mm$^2$. Such low surface energy materials can include, as examples, polyvinyl acetate (PVA), polypropylene (PP), and polytetrafluoroethylene (PTFE).

Other features and aspects of the present disclosure will become apparent by consideration of the detailed description and accompanying drawings.

DETAILED DESCRIPTION

Figure 1:
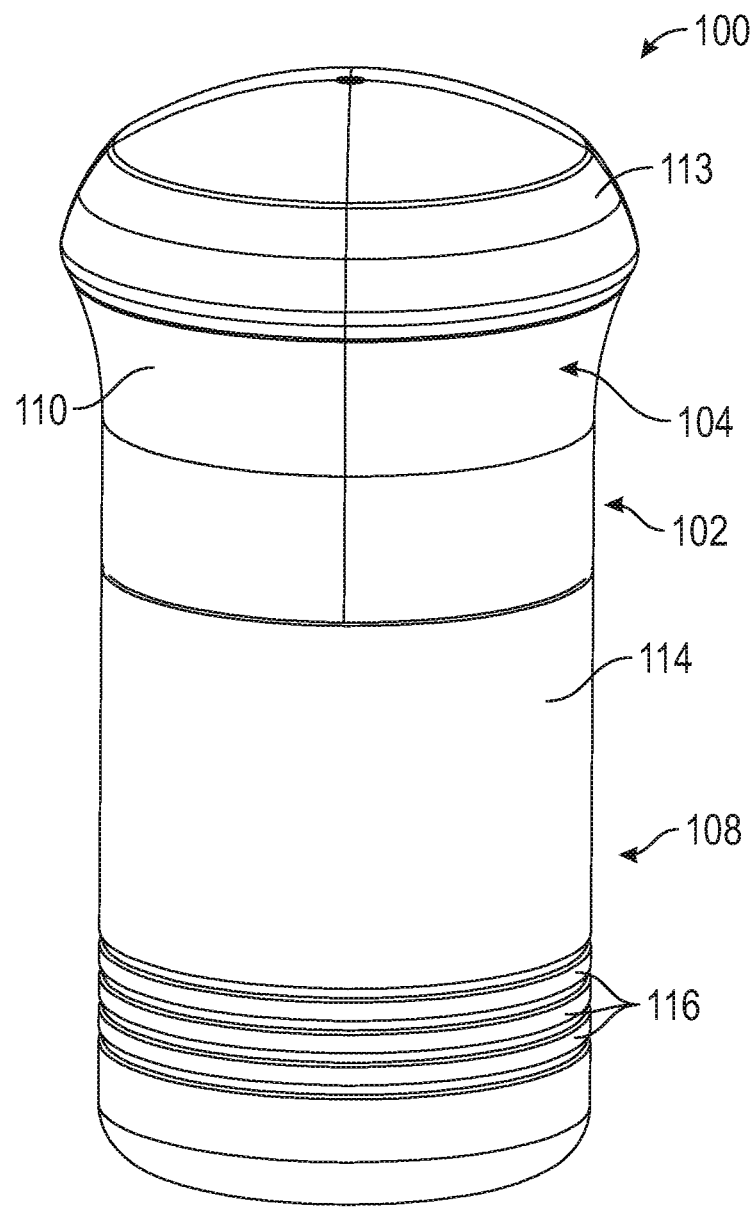
FIG. 1 is a top perspective view of an applicator according to an embodiment of the present disclosure.

Before any embodiments of the present disclosure are explained in detail, it is to be understood that the inventions are not limited in its application to the details of construction and the arrangement of components set forth in the following description or illustrated in the following drawings. The inventions are capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. Furthermore, terms such as "front," "rear," "top," "bottom," "upward," "downward," "under," and the like are only used to describe elements as they relate to one another, but are in no way meant to recite specific orientations of the apparatus, to indicate or imply necessary or required orientations of the apparatus, or to specify how the inventions described herein will be used, mounted, displayed, or positioned in use.

In discussing the applicators of the present disclosure, the term "downward," and variations thereof, is sometimes used to describe the direction in which microneedles are pressed into skin, and "upward" to describe the opposite direction. However, those of skill in the art will understand that the applicators can be used where the microneedles are pressed into skin at an angle to the direction of the earth's gravity, or even in a direction contrary to that of the earth's gravity, and these terms are only used for simplicity and clarity to describe relative directions.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The present disclosure generally relates to an applicator and method for applying a microneedle device, including an array of microneedles, to skin (or a biological membrane) to treat the skin (i.e., create small holes or perforations or micropores in the skin) and/or to deliver an active agent to the skin.

Figure 2:
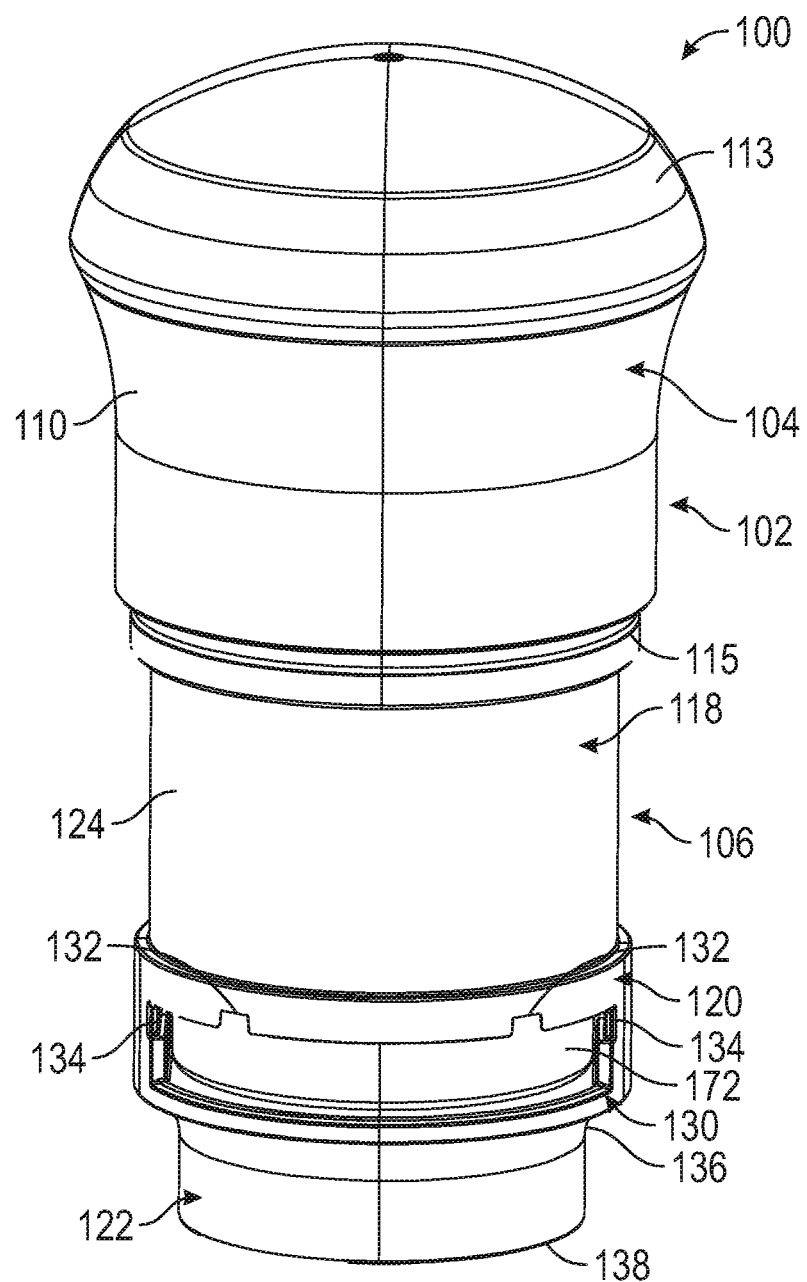
FIG. 2 is a perspective view of the applicator of FIG. 1 with a cover removed.
Figure 3:
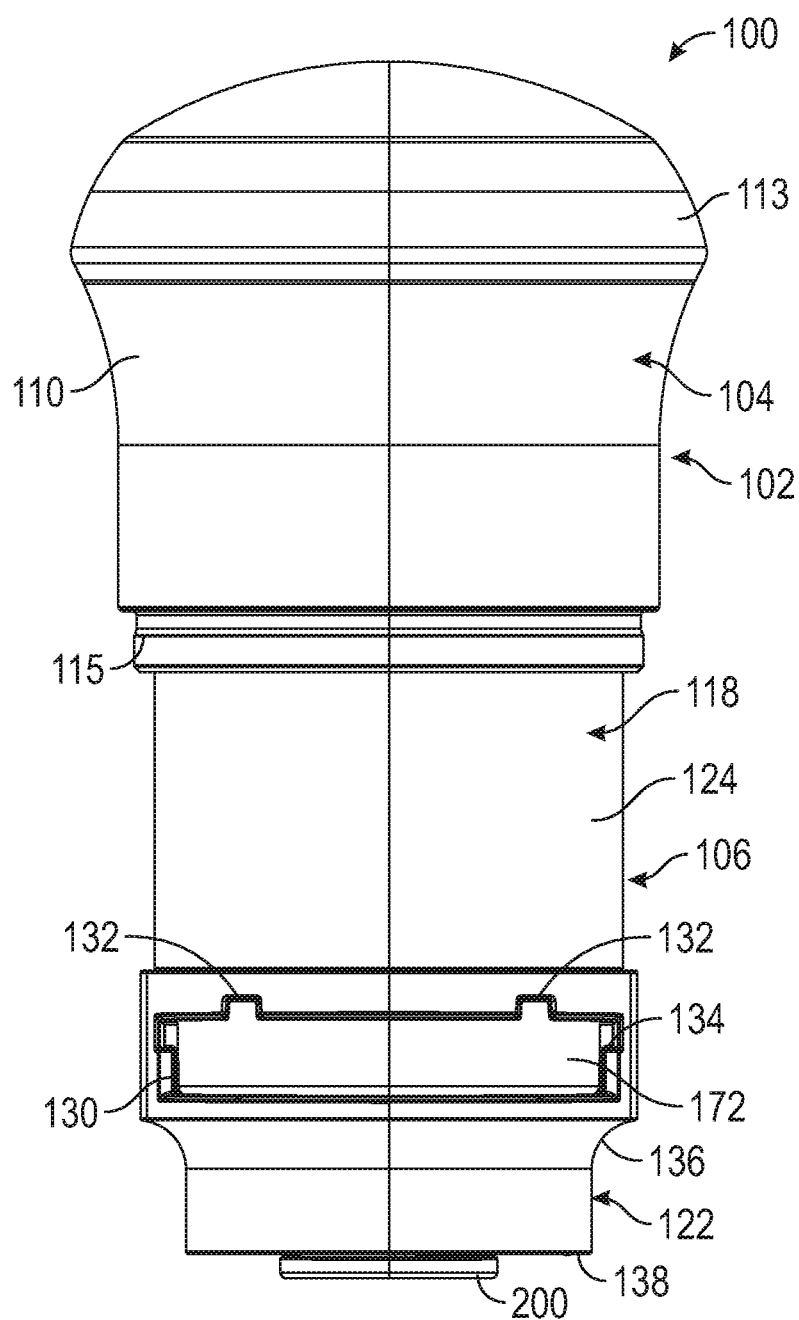
FIG. 3 is a front elevational view of the applicator of FIGS. 1 and 2.

Referring to FIGS. 1-3, in an embodiment, an applicator 100 includes a body 102 having an upper housing 104 and a lower housing 106, and a cover 108 (removed in FIGS. 2 and 3). Upper housing 104 can be ergonomically shaped in a way to enable ease of gripping body 102 by a user—such that it can fit in the palm of a hand and/or a center of gravity of the applicator 100 can be aligned with a center of a hand that is used to grip the applicator 100. Upper housing 104 includes an outer surface 110 and an inner surface 112 (see, for example, FIG. 14). Outer surface 110 can include a matte surface finish or other surface finish to further enable ease of gripping body 102 by a user. In embodiments, upper housing 104 can include a rubber grip material portion or other medical grade material on an outer surface 110 for aesthetic purposes and/or to further enable ease of gripping body 102 by a user. Inner surface 112 of upper housing 104 can include a smooth surface finish or other surface finish, such as one with with a low surface energy, to enable sliding engagement with an outer surface 124 of an upper portion 118 of lower housing 106, which is described in further detail below. In an embodiment, such low surface energy material can preferably comprise a surface energy of less than about 37 mJ/mm$^2$. In an embodiment, such low surface energy material can preferably comprise a surface energy of less than about 29 mJ/mm$^2$. In an embodiment, such low surface energy material can preferably comprise a surface energy of less than about 18 mJ/mJ/mm$^2$. Such low surface energy materials can include polyvinyl acetate (PVA), polypropylene (PP), and polytetrafluoroethylene (PTFE). In an embodiment, upper housing 104 can include a cap 113 or other structure, which can be removable, thus enabling access into and/or covering upper housing 104, such as to access the internal components of applicator 100. In an embodiment, upper housing 104 can be made of polycarbonate/acrylonitrile butadiene styrene (PC/ABS), which can have properties such as low shrink, dimensional stability and structural rigidity. In other embodiments, upper housing 104 can be made of other medical grade engineering plastics having high impact strength.

Cover 108 is designed, configured, and/or shaped to cover, protect, and/or envelop lower housing 106 and enclose internal components of applicator 100 and includes an inner surface (not depicted) and an outer surface 114. Inner surface (not depicted) of cover 108 can include one or more tabs or projections or other structures (not depicted) proximate an open end (not depicted) of the cover 108 to cooperate with a lip 115 or other structure on upper housing 104 or other portion of body 102 to facilitate retaining cover 108 in place on body 102 when applicator 100 is not being used to enclose and/or protect internal components of applicator 100. While such structures inhibit cover 108 from falling off of body 102 when applicator 100 is not being used, a user can manually remove cover 108 when such user desires to use applicator 100. In an embodiment, applicator 100 could include a structure to inhibit cover 108 from being used or opened by unintended or unpermitted users, similar to those used in "child proof" medicine containers. Cover 108 can additionally include one or more ribs or recesses 116, as depicted, or other structure enabling ease of gripping cover 108, but also can serve as aesthetic features. In an embodiment, cover 108 can be made of polycarbonate/acrylonitrile butadiene styrene (PC/ABS), which can have properties such as low shrink, dimensional stability and structural rigidity. In other embodiments, cover 108 can be made of other medical grade engineering plastics having high impact strength.

Referring to FIGS. 2 and 3, lower housing 106 includes an upper portion 118, a middle portion 120, and a lower portion 122. Upper portion 118 of lower housing 106 includes an outer surface 124 that can have a smooth surface finish or other finish with low surface energy to enable sliding engagement with inner surface 112 of upper housing 104. Upper portion 118 of lower housing 106 can further include a return spring recess 126 and a door spring recess 128, described in further detail below. Middle portion 120 of lower housing 106, which can have a bigger diameter than upper portion 118 and lower portion 122 of lower housing 106, can include a slot 130 or opening for insertion of a microneedle array carrier 140, described below. Slot 130 can include one or more guiding structures 132, depicted as notches, in an embodiment, for accurate guiding of a microneedle array carrier 140 into position and to ensure that microneedle array carrier 140 is not inserted into slot 130 in an improper orientation, such as upside down. In another embodiment, guiding structures 132 could include projections projecting into slot 130 as opposed to notches extending away from slot 130. Slot 130 can further include one or more shoulders 134, also enabling accurate guiding of a microneedle array carrier 140 into position and corresponding with the structure of microneedle array carrier 140. Lower portion 122 of lower housing 106 can include a radiused or necked-down portion 136 that can minimize the size of an opening on an underside of lower portion 122, such as to generally correspond with the size of a microneedle array assembly 142, described below, to be applied. Lower portion 122 includes a lower surface 138 on its underside. In an embodiment, lower housing 106 or certain portions of lower housing 106 can be made of polycarbonate/acrylonitrile butadiene styrene (PC/ABS), which can have properties such as low shrink, dimensional stability and structural rigidity. In embodiments, lower housing 106 can be made of other medical grade engineering plastics having high impact strength. In embodiments, an inside surface of lower portion 122 of lower housing 106 can include polypropylene (PP) having beneficial low surface energy properties, which inhibits a microneedle array assembly 142 from sticking to lower housing 106 during application. Such polypropylene structure could be molded into a rigid structure in a two-shot process, configured as a separate component, inserted or fit into a PC/ABS portion, or otherwise formed with or into lower housing 106. In an alternative embodiment, the lower portion 122 of lower housing 106 can have substantially the same diameter as the upper portion 118 of the lower housing 106 so as to provide additional interior clearance for the microneedle array assembly 142 as it exits the device.

Figure 4:
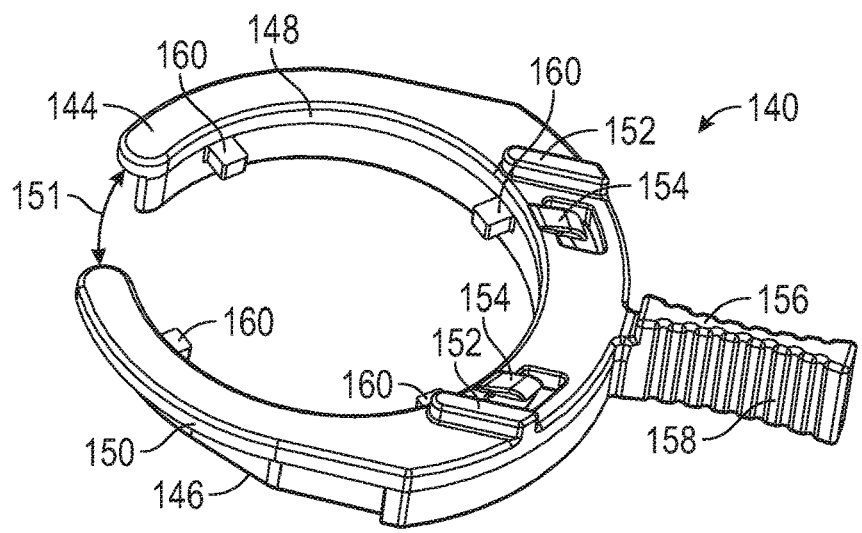
FIG. 4 is a top perspective view of a microneedle array carrier.
Figure 5:
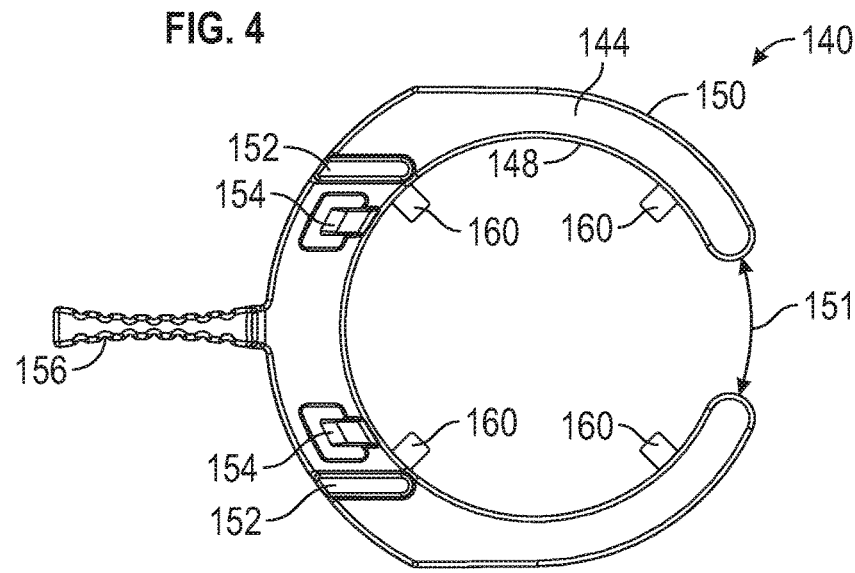
FIG. 5 is a bottom plan view of the microneedle array carrier of FIG. 4.
Figure 6:
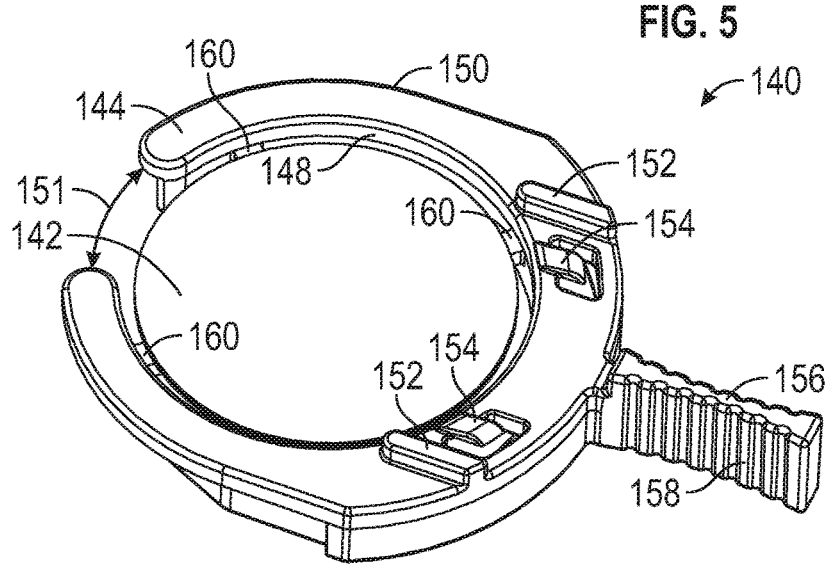
FIG. 6 is a top perspective view of the microneedle array carrier of FIGS. 4 and 5 with a microneedle array.

FIGS. 4-9 depict a microneedle array carrier 140. FIGS. 4 and 5 depict the microneedle array carrier 140 without a microneedle array assembly 142 and FIGS. 6-9 depict microneedle array carrier 140 with a microneedle array assembly 142 disposed on microneedle array carrier 140. Microneedle array carrier 140 includes a top side 144, bottom side 146, inner surface 148, and outer surface 150. Top side can include one or more aligning projections 152 that correspond with guiding structures 132 included in slot 130 on lower housing 106 of body 102. In embodiments, wherein guiding structures 132 are formed as projections, as opposed to notches, aligning projections 152 can be recesses or notches in carrier as opposed to projections or fins. The aligning projections 152 can be substantially the same with as the microneedle array carrier 140. In an additional embodiment, the aligning projections can be shorter than the width of the microneedle array carrier 140. Microneedle array carrier 140 can further include one or more securing tabs 154 or projections on top surface 144, as depicted, or bottom surface 146 to enable a snug fit between microneedle array carrier 140 and slot 130 when microneedle array carrier 140 is positioned in slot 130.

Microneedle array carrier 140 can include a handle or grip portion 156 so that microneedle array carrier 140 can be easily removed from any packaging, carried, and positioned in applicator 100, such as into slot 130. Handle 156 can include structure, such as ribbing 158 or other surface features or finishes, to enhance ease of gripping microneedle array carrier 140. The grip portion 156 can additionally include rounded edges as to be more ergonomically favorable to users with sensitive fingers.

Microneedle array carrier 140 can include one or more tabs or projections 160, such as extending from inner surface 148. As depicted in FIGS. 6-9, microneedle array assembly 142 can be placed on projections 160. In this embodiment, as described below, microneedle array assembly 142 can include an adhesive, such as pressure sensitive adhesive (PSA) on an underside 167 of a substrate 166 that is in contact with projections 160 to retain microneedle array assembly 142 on projections 160. In an embodiment, projections 160 can be configured or sized such that, while retaining microneedle array assembly 142 on projections 160, upon delivery, there is a minimal amount of resistance to microneedle array assembly 142 being removed from projections 160 enabling efficacious delivery of a microneedle array assembly 142 onto skin during application with applicator 100.

Microneedle array carrier 140 can accommodate further efficacious delivery of a microneedle array assembly 142 onto skin during application with applicator 100 by providing a rigid structure to provide symmetric hold and release forces minimizing deflection of the projections 160 during microneedle array assembly 142 release from projections 160. Also, using a low surface energy material for microneedle array carrier 140, specifically, for projections 160, can be provided to accommodate microneedle array assembly 142 hold and release during manufacturing, packaging and microneedle array assembly 142 delivery. The external structure of microneedle array carrier 140 can be made of an engineering plastic with beneficial properties such as low shrink, stable dimensions, and rigidity. Projections 160 and inner surface 148 of microneedle array carrier 140 can be made of polypropylene, which can provide the benefit of having a low surface energy, which accommodates microneedle array assembly 142 release from projections 160, pick and place during drug coating, and microneedle array assembly 142 delivery to the skin during application. Other engineering plastics may also be used for microneedle array carrier 140. In an embodiment, such low surface energy material can preferably comprise a surface energy of less than about 37 $mJ/mm^2$. In an embodiment, such low surface energy material can preferably comprise a surface energy of less than about 29 $mJ/mm^2$. In an embodiment, such low surface energy material can preferably comprise a surface energy of less than about 18 $mJ/mJ/mm^2$. Such low surface energy materials can include polyvinyl acetate (PVA), polypropylene (PP), and polytetrafluoroethylene (PTFE).

Referring to FIGS. 4-9, a gap 151 in microneedle array carrier 140 can be included and can be dimensioned to be larger than a width 195 or diameter of plunger post 194. This can enable removal of the array carrier 140 after plunger 174 has been fired, as discussed below, which can enable a user to store applicator 100 between uses in an unprimed state or configuration. In an embodiment, microneedle array carrier 140 is generally in the shape of a ring with gap 151 in the ring shape. Microneedle array assembly 140 can be positioned between the inner surfaces of the ring or border. In embodiments, gap 151 is larger than a width or diameter of plunger post 194. In embodiments, gap 151 is initially slightly smaller than a width or diameter of plunger post 194 but is comprised of flexible material such that gap 151 can be flexed to be larger than a width or diameter of plunger post 194.

Referring to FIGS. 10-13, depicting a microneedle array assembly 142, which can also be referred to herein as a "microneedle device" or "patch" and can include the array 162 of microneedles 164 (or, collectively, the "microneedle array") and any supporting structure or substrate 166 used to support microneedle array 162 and/or to couple microneedle array 162 to other structures or components of applicator 100, such as projections 160.

As mentioned above, in some embodiments, active ingredients or agents (e.g., drugs) can be delivered via the microneedles 164 (e.g., via solid or hollow microneedles, as described below). Examples of pharmaceutically active agents (also referred to as "drugs") that can be incorporated into the applicators of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; anti-obesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the microneedles 164 (e.g., via solid or hollow microneedles, as described below). Examples of peptide therapeutic agents that can be incorporated into the applicators of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e.g. IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Patent Application Publication No. 2004/0049150 (Dalton et al.), the disclosure of which is hereby incorporated by reference in its entirety.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

Microneedle arrays 162 useful for practicing the present disclosure can have a variety of configurations and features, such as those described in the following patents and patent applications, the disclosures of which are incorporated herein by reference in their entirety. One embodiment for the microneedle arrays 162 includes the structures disclosed in U.S. Patent Application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin. Still another embodiment for the microneedle arrays includes the structures disclosed in U.S. Pat. No. 6,312,612 (Sherman et al.), which describes tapered structures having a hollow central channel Yet still another embodiment for the microneedle arrays includes the structures disclosed in U.S. Pat. No. 6,379,324 (Gartstein et al.), which describes hollow microneedles having at least one longitudinal blade at the top surface of the tip of the microneedle. A further embodiment for the microneedle arrays includes the structures disclosed in U.S. Patent Application Publication Nos. US2012/0123387 (Gonzalez et al.) and US2011/0213335 (Burton et al.), which both describe hollow microneedles. A still further embodiment for the microneedle arrays includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO2012/074576 (Duan et al.), which describes liquid crystalline polymer (LCP) microneedles; and PCT Publication No. WO2012/122162 (Zhang et al.), which describes a variety of different types and compositions of microneedles that can be employed in the microneedles of the present disclosure.

In some embodiments, the microneedle material can be (or include) silicon, glass, or a metal such as stainless steel, titanium, or nickel titanium alloy. In some embodiments, the microneedle material can be (or include) a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In some embodiments, the microneedles can be made from (or include) a combination of two or more of any of the above-mentioned materials. For example, the tip of a microneedle may be a dissolvable material, while the remainder of the microneedle is a medical grade polymeric material.

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). In a preferred embodiment, the plurality of microneedles in a microneedle array each have a square pyramidal shape.

In some embodiments, the plurality of microneedles in a microneedle array are solid microneedles (that is, the microneedles are solid throughout). In some embodiments, the plurality of solid microneedles in a solid microneedle array can have a square pyramidal shape, triangular pyramidal shape, stepped pyramidal shape, conical shape, or microblade shape. In a preferred embodiment, the plurality of solid microneedles in a solid microneedle array each have a square pyramidal shape.

In some embodiments, the plurality of microneedles in a microneedle array are hollow microneedles (that is, the microneedles contain a hollow bore through the microneedle). The hollow bore can be from the base of the microneedle to the tip of the microneedle or the bore can be from the base of the microneedle to a position offset from the tip of the microneedle. In some embodiments, one or more of the plurality of hollow microneedles in a hollow microneedle array can have a conical shape, cylindrical shape, square pyramidal shape, triangular pyramidal shape, or the shape of a hypodermic needle.

In some embodiments, one or more of the plurality of hollow microneedles in a hollow microneedle array can have a conical shape. In some embodiments, one or more of the plurality of hollow microneedles in a hollow microneedle array can have a cylindrical shape. In some embodiments, one or more of the plurality of hollow microneedles in a hollow microneedle array can have a square pyramidal shape. In some embodiments, one or more of the plurality of hollow microneedles in a hollow microneedle array can have a triangular pyramidal shape. In some embodiments, one or more of the plurality of hollow microneedles in a hollow microneedle array can have the shape of a hypodermic needle. In a preferred embodiment, the plurality of hollow microneedles in a hollow microneedle array each have the shape of a conventional hypodermic needle.

Figure 13:
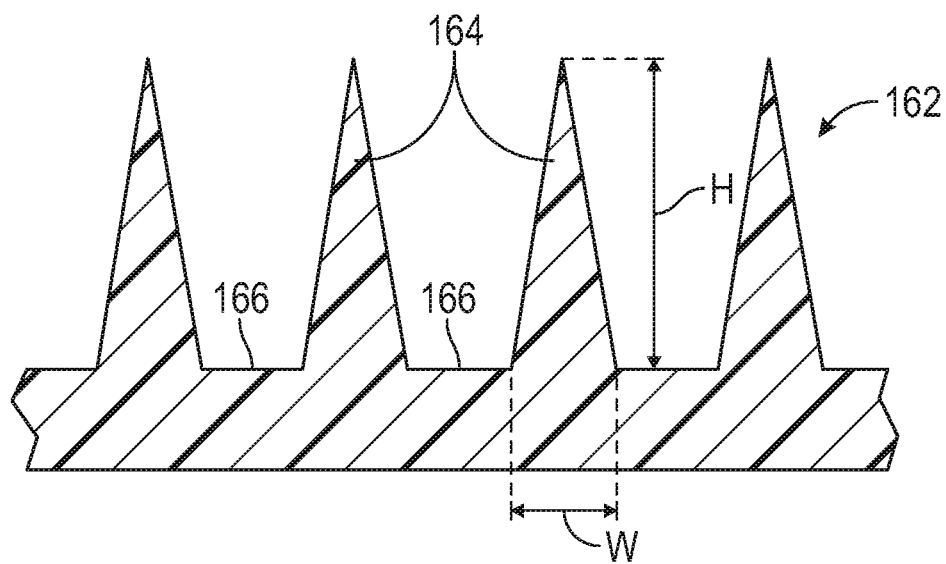
FIG. 13 is a close-up side elevational view of a microneedle array (shown with the microneedles pointing upwardly).

FIG. 13 shows a portion of the microneedle array 162 that includes four microneedles 164 positioned on a substrate 166. Each microneedle 164 has a height h, which is the length from the tip of the microneedle 164 to the microneedle 164 base at substrate 166. Either the height of a single microneedle 164 or the average height of all microneedles 164 on the microneedle array 162 can be referred to as the height of the microneedle, h. In some embodiments, each of the plurality of microneedles 164 (or the average of all of the plurality of microneedles 164) has a height of about 100 to about 3000 micrometers, in some embodiments, about 100 to about 1500 micrometers, in some embodiments, about 100 to about 1200 micrometers, and, in some embodiments, about 100 to about 1000 micrometers.

In some embodiments, each of the plurality of microneedles 164 (or the average of all of the plurality of microneedles 164) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1500 micrometers, about 500 to about 1000 micrometers, or about 500 to about 750 micrometers.

In some embodiments, each of the plurality of microneedles 164 (or the average of all of the plurality of microneedles 164) has a height of about 800 to about 1400 micrometers.

In some embodiments, each of the plurality of microneedles 164 (or the average of all of the plurality of microneedles 164) has a height of about 500.

In some embodiments, each of the plurality of microneedles 164 (or the average of all of the plurality of microneedles 164) has a height of less than about 3000 micrometers. In other embodiments, each of the plurality of microneedles 164 (or the average of all of the plurality of microneedles 164) has a height of less than about 1500 micrometers. In still other embodiments, each of the plurality of microneedles 164 (or the average of all of the plurality of microneedles 164) has a height of less than about 1200 micrometers. In yet still other embodiments, each of the plurality of microneedles 164 (or the average of all of the plurality of microneedles 164) has a height of less than about 1000 micrometers. In further embodiments, each of the plurality of microneedles 164 (or the average of all of the plurality of microneedles 164) has a height of less than about 750 micrometers. In still further embodiments, each of the plurality of microneedles 164 (or the average of all of the plurality of microneedles 164) has a height of less than about 600 micrometers.

In some embodiments, each of the plurality of microneedles 164 (or the average of all of the plurality of microneedles 164) has a height of at least about 100 micrometers. In other embodiments, each of the plurality of microneedles 164 (or the average of all of the plurality of microneedles 164) has a height of at least about 200 micrometers. In still other embodiments, each of the plurality of microneedles 164 (or the average of all of the plurality of microneedles 164) has a height of at least about 250 micrometers. In further embodiments, each of the plurality of microneedles 164 (or the average of all of the plurality of microneedles 164) has a height of at least about 500 micrometers. In still further embodiments, each of the plurality of microneedles 164 (or the average of all of the plurality of microneedles 164) has a height of at least about 800 micrometers.

In some embodiments employing solid microneedles 164, each of the plurality of solid microneedles 164 (or the average of all of the plurality of solid microneedles) has a height of about 100 to about 1500 micrometers, about 100 to about 1200 micrometers, about 200 to about 1000 micrometers, about 200 to about 750 micrometers, about 200 to about 600 micrometers, or about 500 micrometers.

In some embodiments employing hollow microneedles, each of the plurality of hollow microneedles (or the average of all of the plurality of hollow microneedles) has a height of about 100 to about 3000 micrometers, about 800 to about 1400 micrometers, or about 500 micrometers.

In some embodiments, each of the plurality of hollow microneedles (or the average of all of the plurality of hollow microneedles) has a height of about 900 to about 1000 micrometers. In other embodiments, each of the plurality of hollow microneedles (or the average of all of the plurality of hollow microneedles) has a height of about 900 to about 950 micrometers. In still other embodiments, each of the plurality of hollow microneedles (or the average of all of the plurality of hollow microneedles) has a height of about 900 micrometers.

Figure 7:
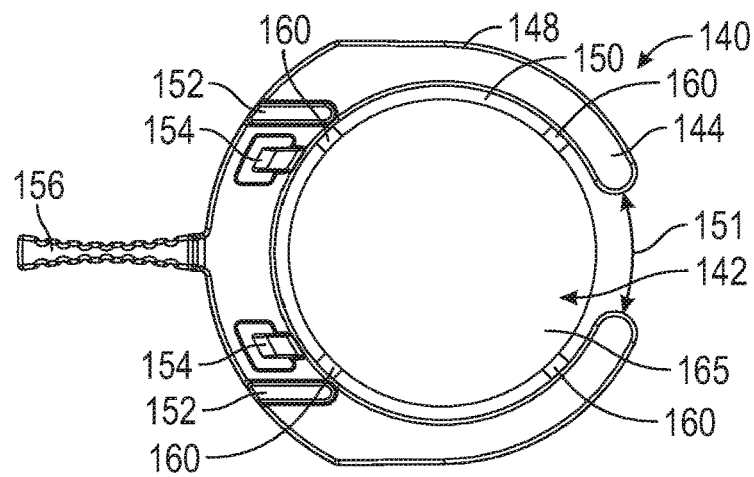
FIG. 7 is a top plan view of the microneedle array carrier of FIG. 6.
Figure 8:
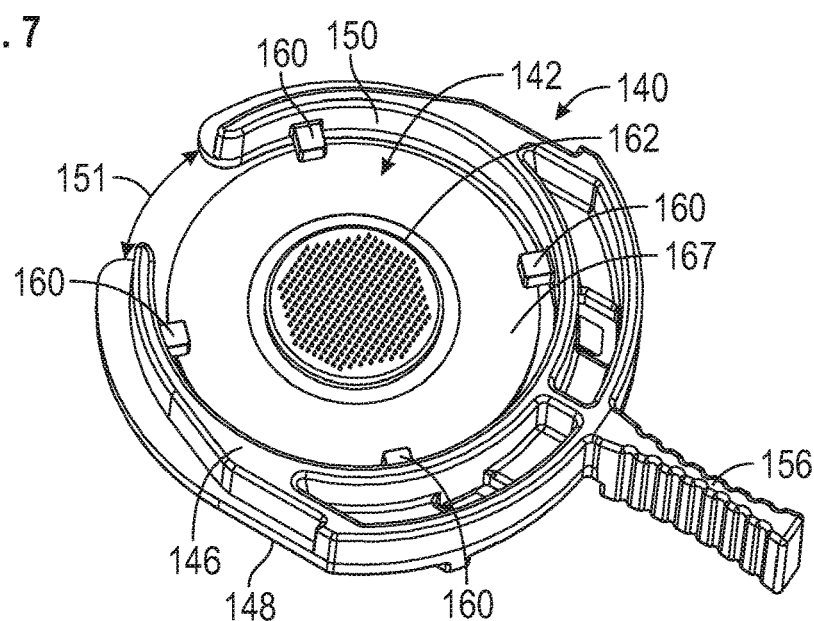
FIG. 8 is a bottom perspective view of the microneedle array carrier of FIG. 6.
Figure 9:
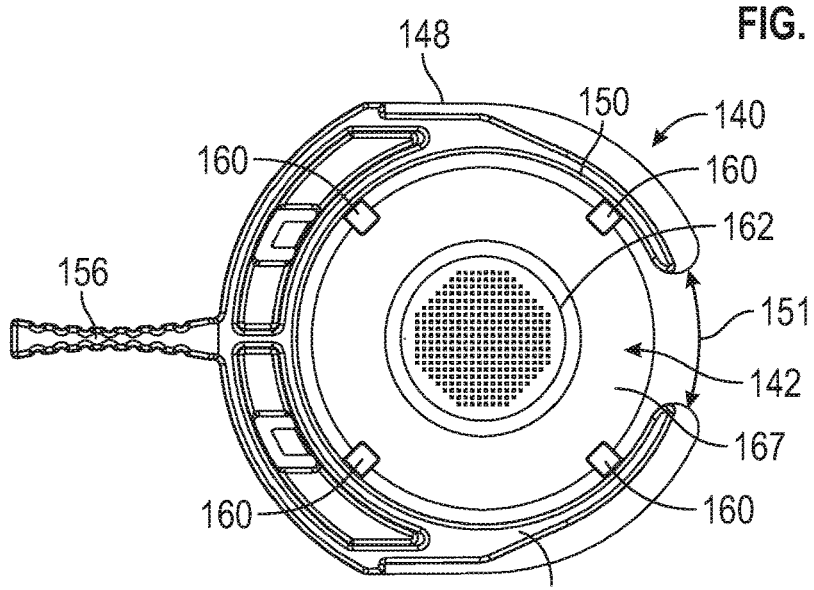
FIG. 9 is a bottom plan view of the microneedle array carrier of FIG. 6.
Figure 10:
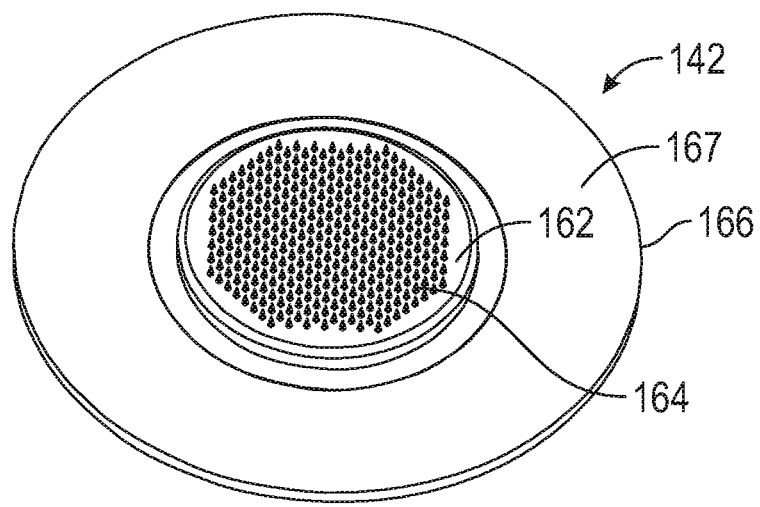
FIG. 10 is a bottom perspective view of a microneedle device according to one embodiment of the present disclosure.
Figure 11:
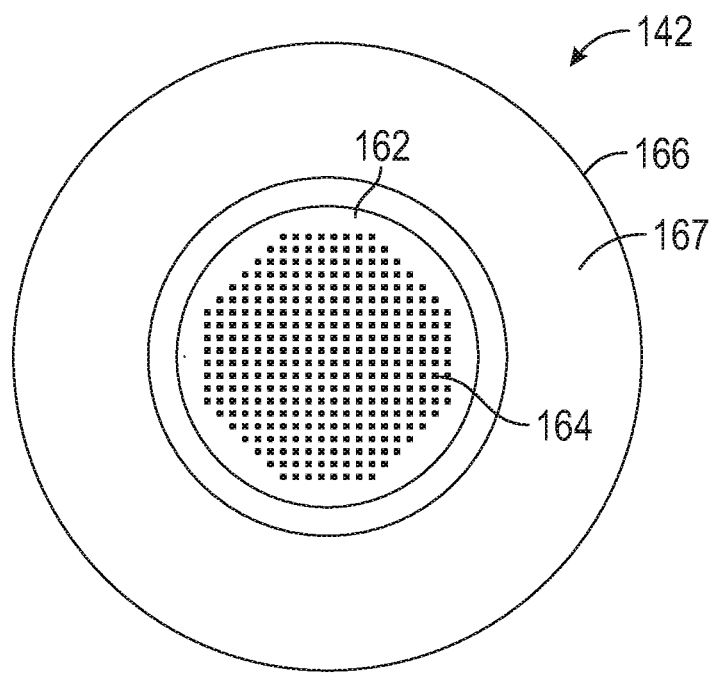
FIG. 11 is a bottom plan view of the microneedle device of FIG. 10.
Figure 12:
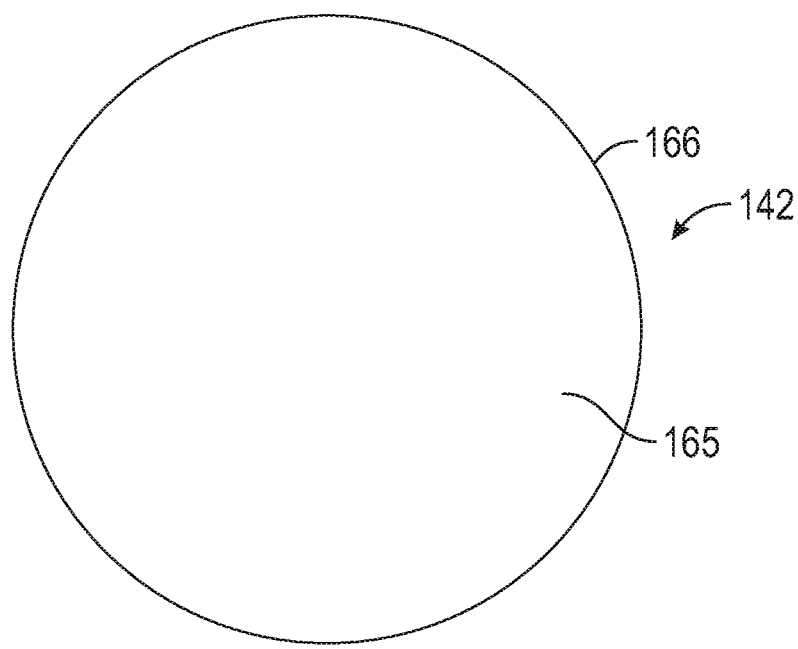
FIG. 12 is a top plan view of the microneedle device of FIG. 10.

A single microneedle or the plurality of microneedles 164 in a microneedle array can also be characterized by their aspect ratio. The aspect ratio of a microneedle is the ratio of the height of the microneedle, h to the width (at the base of the microneedle), w (as shown in FIG. 7). The aspect ratio can be presented as h:w. In some embodiments, each of the plurality of microneedles 164 (or the average of all the plurality of microneedles 164) has (have) an aspect ratio in the range of 2:1 to 5:1. In some of these embodiments, each of the plurality of microneedles 164 (or the average of all of the plurality of microneedles 164) has (have) an aspect ratio of at least 3:1.

In some embodiments, the array of microneedles 164 contains about 100 to about 1500 microneedles per $cm^2$ of the array of microneedles.

In some embodiments employing solid microneedles, the array of solid microneedles contains about 100 to about 1500 solid microneedles per $cm^2$ of the array of solid microneedles.

In some embodiments, the array of solid microneedles contains about 200 to about 500 solid microneedles per $cm^2$ of the array of solid microneedles.

In some embodiments, the array of solid microneedles contains about 300 to about 400 solid microneedles per $cm^2$ of the array of solid microneedles.

In some embodiments employing hollow microneedles, the array of hollow microneedles contains about 3 to about 30 hollow microneedles per array of hollow microneedles.

In some embodiments, the array of hollow microneedles contains about 10 to about 30 hollow microneedles per array of hollow microneedles.

In some embodiments, the array of hollow microneedles contains about 3 to about 20 hollow microneedles per array of hollow microneedles.

In some embodiments, the array of hollow microneedles contains about 13 to about 20 hollow microneedles per array of hollow microneedles.

In some embodiments, the array of hollow microneedles contains about 8 to about 18 hollow microneedles per array of hollow microneedles.

In some embodiments, the array of hollow microneedles contains about 18 hollow microneedles per array of hollow microneedles.

In some embodiments, the array of hollow microneedles contains about 12 hollow microneedles per array of hollow microneedles.

In some embodiments, each of the plurality of microneedles (or the average of all of the plurality of microneedles) in a microneedle array can penetrate into the skin to a depth of about 50 to about 1500 micrometers, about 50 to about 400 micrometers, or about 50 to about 250 micrometers.

In some embodiments, each of the plurality of microneedles (or the average of all of the plurality of microneedles) in a microneedle array can penetrate into the skin to a depth of about 100 to about 400 micrometers, or about 100 to about 300 micrometers.

In some embodiments, each of the plurality of microneedles (or the average of all of the plurality of microneedles) in a microneedle array can penetrate into the skin to a depth of about 150 to about 1500 micrometers, or about 800 to about 1500 micrometers.

In some embodiments, each of the plurality of microneedles (or the average of all of the plurality of microneedles) in a microneedle array can penetrate into the skin to a depth of about 400 to about 800 micrometers.

For all of the above embodiments, it will be appreciated that the depth of penetration (DOP) of each of the plurality of microneedles (or the average of all of the plurality of microneedles) in a microneedle array may not be the full length of the microneedles themselves.

In some embodiments, the microneedle array assembly 142 according to the present disclosure can be in the form of a patch. One example of such an embodiment is shown in more detail in FIG. 10-12. Microneedle array assembly 142 includes a microneedle array 162, pressure sensitive adhesive presented on a substrate 166. Microneedle array 162 is illustrated with microneedles 164 protruding from microneedle substrate 166. Microneedles 164 can be arranged in any desired pattern or distributed over substrate 166 randomly. As shown, microneedles 164 are arranged in uniformly spaced rows. When arranged in rows, the rows can be arranged so that microneedles 164 are aligned or offset. In some embodiments (not shown), microneedles 164 can be arranged in a polygonal pattern such as a triangle, square, rectangle, pentagon, hexagon, heptagon, octagon, or trapezoid. In other embodiments (not shown), microneedles 164 can be arranged in a circular or oval pattern.

In some embodiments, the surface area of the substrate covered with microneedles is about 0.1 cm$^2$ to about 20 cm$^2$. In some of these embodiments, the surface area of the substrate covered with microneedles is about 0.5 cm$^2$ to about 5 cm$^2$. In some other of these embodiments, the surface area of the substrate covered with microneedles is about 1 cm$^2$ to about 3 cm$^2$. In still other of these embodiments, the surface area of the substrate covered with microneedles is about 1 cm$^2$ to about 2 cm$^2$.

In some embodiments, the microneedles of the present disclosure can be disposed over substantially the entire surface of the array. In other embodiments (not shown), a portion of the substrate may not be provided with microneedles (that is, a portion of the substrate is non-structured). In some of these embodiments, the non-structured surface has an area of more than about 1 percent and less than about 75 percent of the total area of the device surface that faces the skin surface. In another of these embodiments, the non-structured surface has an area of more than about 0.65 cm$^2$ (0.10 square inch) to less than about 6.5 cm$^2$ (1 square inch).

For hollow microneedles, a hollow channel or bore extends through the substrate and microneedles. In some embodiments, the bore exits at a channel opening at or near the tip of the hollow microneedle. The channel preferably exits at an opening near the tip of the hollow microneedle. Most preferably, the channel or bore continues along a central axis of the microneedle, but exits similar to a hypodermic needle on a sloping side-wall of the microneedle to help prevent blockage of the channel by tissue upon insertion. In some embodiments, the diameter of the channel bore is about 10 to about 200 micrometers. In other embodiments, the diameter of the channel bore is about 10 to about 150 micrometers. In still other embodiments, the diameter of the channel bore is about 30 to about 60 micrometers.

In some embodiments of hollow microneedles, the average cross-sectional area of the channel bore is about 75 to about 32,000 micrometers. In other embodiments of hollow microneedles, the average cross-sectional area of the channel bore is about 75 to about 18,000 micrometers. In still other embodiments of hollow microneedles, the average cross-sectional area of the channel bore is about 700 to about 3,000 micrometers.

In some embodiments of hollow microneedle arrays, the average spacing between adjacent microneedles (as measured from microneedle tip to microneedle tip) is between about 0.7 mm and about 20 mm. In other embodiments of hollow microneedle arrays, the average spacing between adjacent microneedles is between about 0.7 mm and about 10 mm. In still other embodiments of hollow microneedle arrays, the average spacing between adjacent microneedles is between about 2 mm and about 20 mm. In still other embodiments of hollow microneedle arrays, the average spacing between adjacent microneedles is between about 2 mm and about 10 mm. In a preferred embodiment of hollow microneedle arrays, the average spacing between adjacent microneedles is between about 2 mm.

In some embodiments of hollow microneedle arrays, the average spacing between adjacent microneedles (as measured from microneedle tip to microneedle tip) is greater than about 0.7 mm. In other embodiments of hollow microneedle arrays, the average spacing between adjacent microneedles is greater than about 2 mm.

In some embodiments of hollow microneedle arrays, the average spacing between adjacent microneedles is less than about 20 mm. In other embodiments of hollow microneedle arrays, the average spacing between adjacent microneedles is less than about 10 mm.

In some embodiments of solid microneedle arrays, the average spacing between adjacent microneedles (as measured from microneedle tip to microneedle tip) is between about 200 micrometers and about 2000 micrometers. In other embodiments of solid microneedle arrays, the average spacing between adjacent microneedles is between about 200 micrometers and about 600 micrometers. In still other embodiments of solid microneedle arrays, the average spacing between adjacent microneedles is between about 200 micrometers and about 300 micrometers. In yet still other embodiments of solid microneedle arrays, the average spacing between adjacent microneedles is between about 500 micrometers and about 600 micrometers.

In some embodiments of solid microneedle arrays, the average spacing between adjacent microneedles (as measured from microneedle tip to microneedle tip) is greater than about 200 micrometers. In other embodiments of solid microneedle arrays, the average spacing between adjacent microneedles is greater than about 500 micrometers.

In some embodiments of solid microneedle arrays, the average spacing between adjacent microneedles is less than about 2000 micrometers. In other embodiments of solid microneedle arrays, the average spacing between adjacent microneedles is less than about 1000 micrometers. In still other embodiments of solid microneedle arrays, the average spacing between adjacent microneedles is less than about 600 micrometers. In yet still other embodiments of solid microneedle arrays, the average spacing between adjacent microneedles is less than about 300 micrometers.

The microneedle arrays can be manufactured in any suitable way such as by injection molding, compression molding, metal injection molding, stamping, photolithography, or extrusion. In one embodiment, hollow microneedle arrays can be made by injection molding of a polymer such as medical grade polycarbonate or LCP, followed by laser drilling to form the channels of the microneedles.

Figure 14:
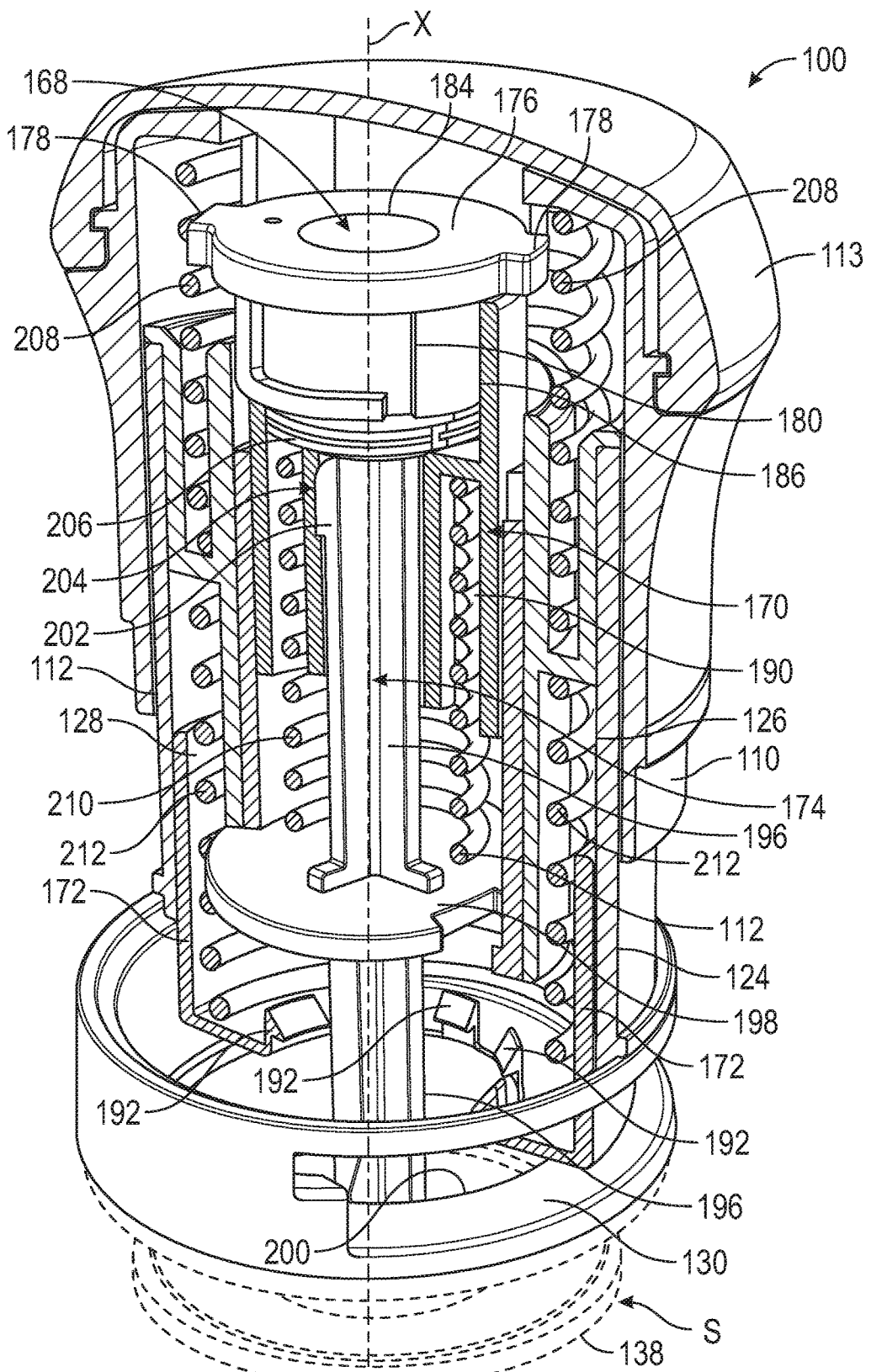
FIG. 14 is a top front perspective and partial cross-sectional view of an applicator according to one embodiment of the present disclosure.

Referring to FIGS. 14-20, in embodiments, applicator 100 includes a latch 168, sleeve 170, door 172, plunger 174, and various springs or other biasing members. Latch 168 can be generally cylindrical in shape and can include an upper flange portion 176 with one or more tabs 178 extending from upper flange portion 176. Latch 168 can include a recess 180 defined in an outer surface 182 of latch 168. Latch 168 can include a latch bore 184 or aperture defined about an axis thereof having a catch 185 therein (see FIGS. 21-26), the axis being coaxial with axis X of applicator 100 (FIG. 14).

Sleeve 170 can be generally cylindrical in shape and include a latch recess 186 on a top side 186 and a sleeve bore 188 or aperture defined about an axis thereof, the axis being coaxial with axis X of applicator 100 (FIG. 14). Sleeve can further include a firing spring recess 190 defined on an underside thereof.

Door 172 can be generally cylindrical in shape and can include one or more tabs 192 or latches proximate a lower end thereof. In embodiments, door 172 can be a desired color or include indicia on a lower end thereof such that a user can easily observe when door 172 is open or closed in operation, as discussed below.

Plunger 174 can include a plunger post 194 having a width 195 or diameter, which post 194, can include one or more fins 196 (in an embodiment, such as that depicted in FIGS. 14-24), a first plunger disc 198, and a second plunger disc 200 proximate a lower end thereof. Plunger can include a tab 202 or latch proximate an upper end 204 thereof. In an embodiment, such as that depicted in FIGS. 27 and 28, plunger post 194 does not comprise fins 196, but rather is generally cylindrical in shape and comprises two cammed tabs 202, which are described further below.

Applicator 100 springs can include a latch spring 206 disposed proximate latch 168, such as depicted underneath latch 168, and cooperating with latch 168 and sleeve 170; return spring 208 disposed proximate upper housing 104 and lower housing 106 and positioned in return spring recess 126 defined in lower housing 106; insertion or firing spring 210 disposed proximate sleeve 170 and first plunger disc 198 presented on plunger 174, positioned in firing spring recess 190 defined in sleeve 170; and door spring 212 disposed proximate lower housing 106 and door 172 and positioned in door spring recess 128 defined in lower housing 106. In embodiments, biasing members other than compression springs, such as leaf springs, rubber members, or structures, can be used in place of or alternative to compression springs.

In embodiments, latch 168, sleeve 170, and plunger 174 can be made of polyoxymethyelene (POM) engineering thermoplastic. Such POM could include Hostaform® MT® SlideX™ 1203 Celanese or Delrin® from DuPont™. In other embodiments, latch 168, sleeve 170, and plunger 174 could be made of other medical grade engineering plastics.

In embodiments, latch spring 206, return spring 208, firing spring 210, and door spring 212 can be made of stainless steel type 302. In other embodiments, latch spring 206, return spring 208, firing spring 210, and door spring 212 could be made of other materials suitable for medical devices.

In embodiments, door 172 is made of a material including high impact strength, such as PC/ABS, such as SABIC Cycoloy® HC1204HF. In other embodiments, door 172 could be made of other medical grade engineering plastics.

Referring to FIG. 14, in use, lower surface 138 of lower portion 122 of lower housing 106 is placed in contact with the skin or another surface, such as a sterile or sanitary surface "S." Upper housing 104 is pushed down axially along an axis X of applicator 100 such that inner surface 112 of upper housing 104 slides over outer surface 124 of lower housing 106 and firing spring 210 is compressed and, thus, energized. This energized firing spring 210 is later used to drive microneedle array assembly 142 from applicator 100.

Figure 15:
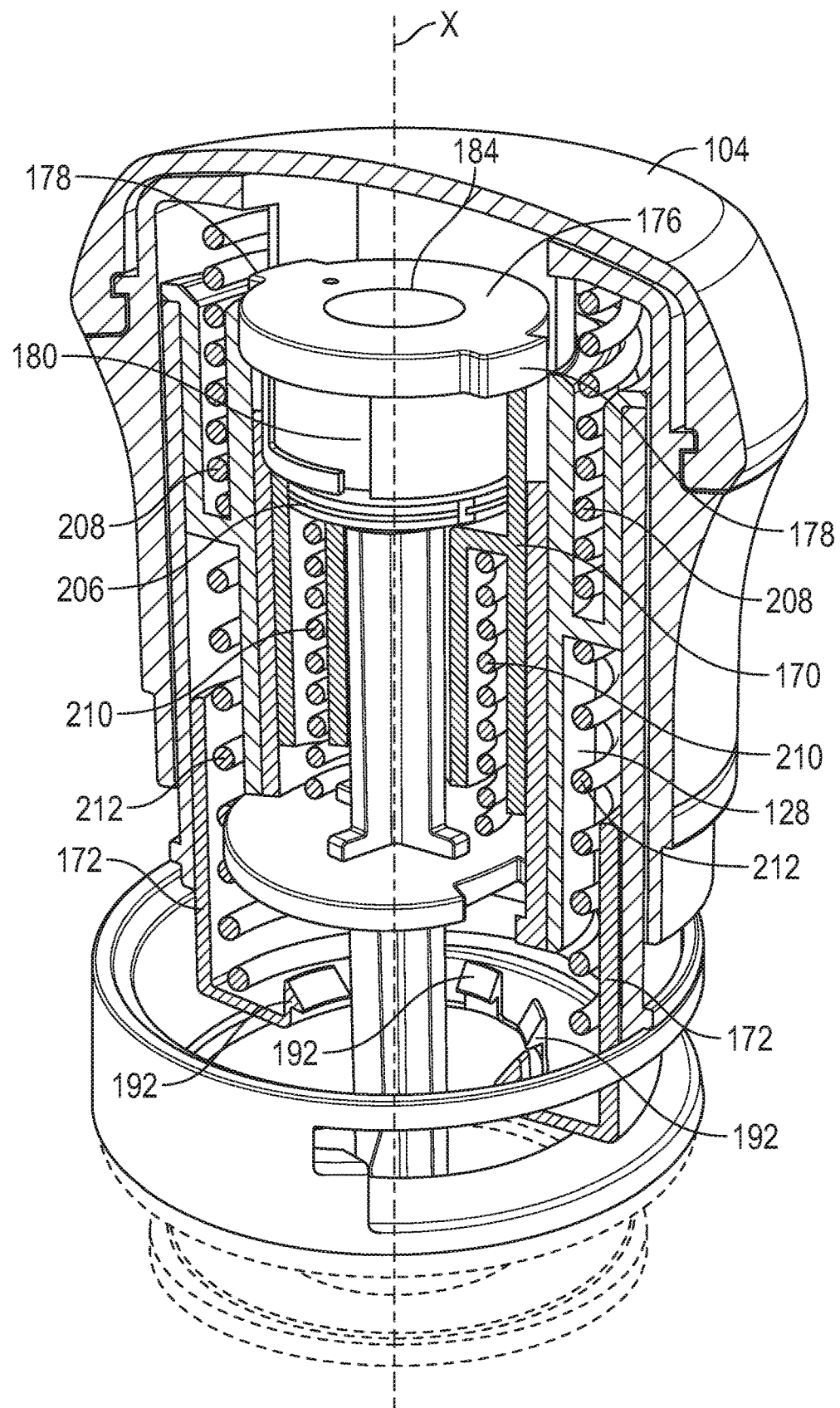
FIG. 15 is a top front perspective and partial cross-sectional view of the applicator of FIG. 14.
Figure 25:
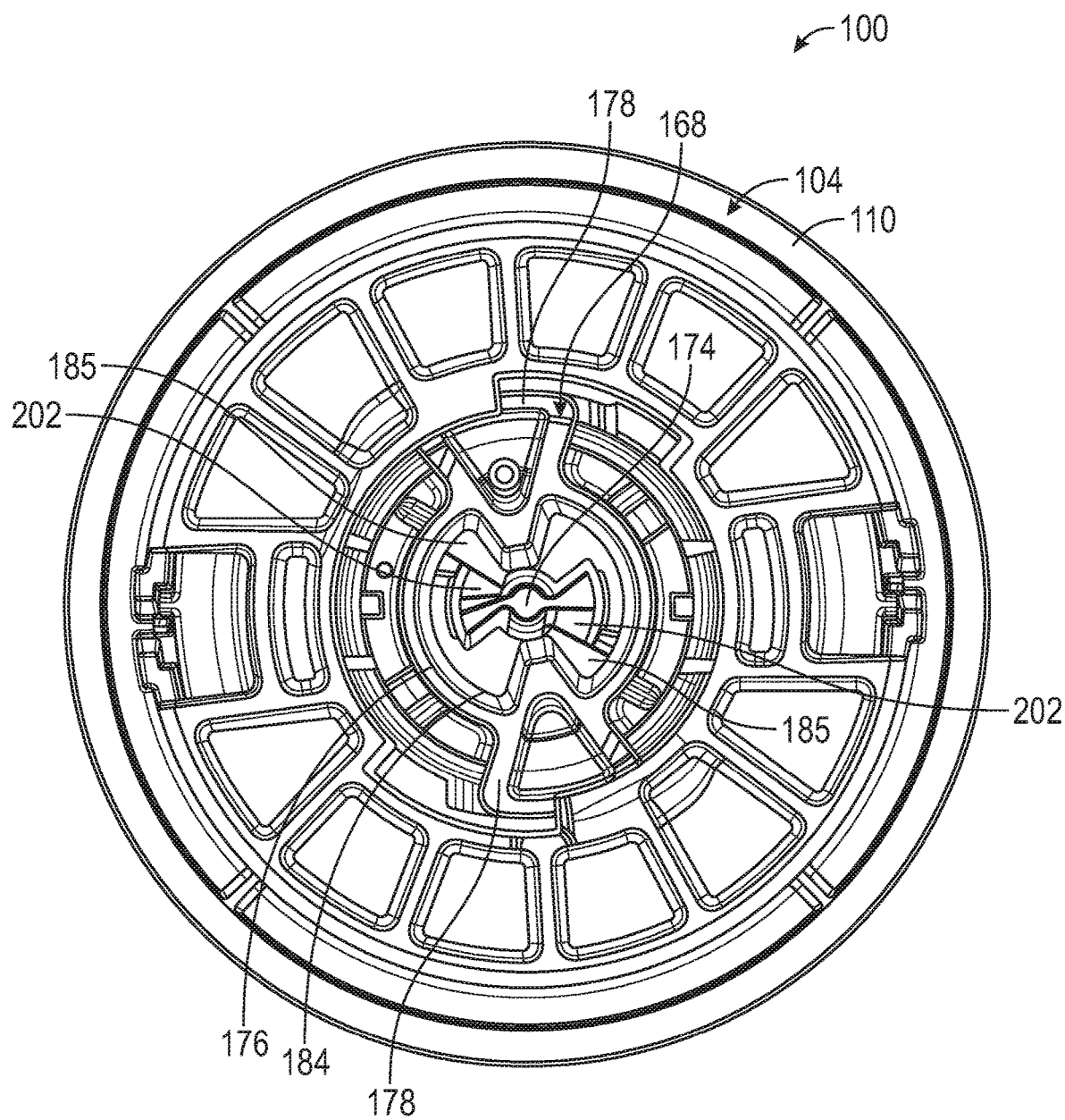
FIG. 25 is a first top plan view of an applicator according to an embodiment of the present disclosure with a cap of upper housing removed to depict a latch and upper portion of a plunger mechanism.
Figure 26:
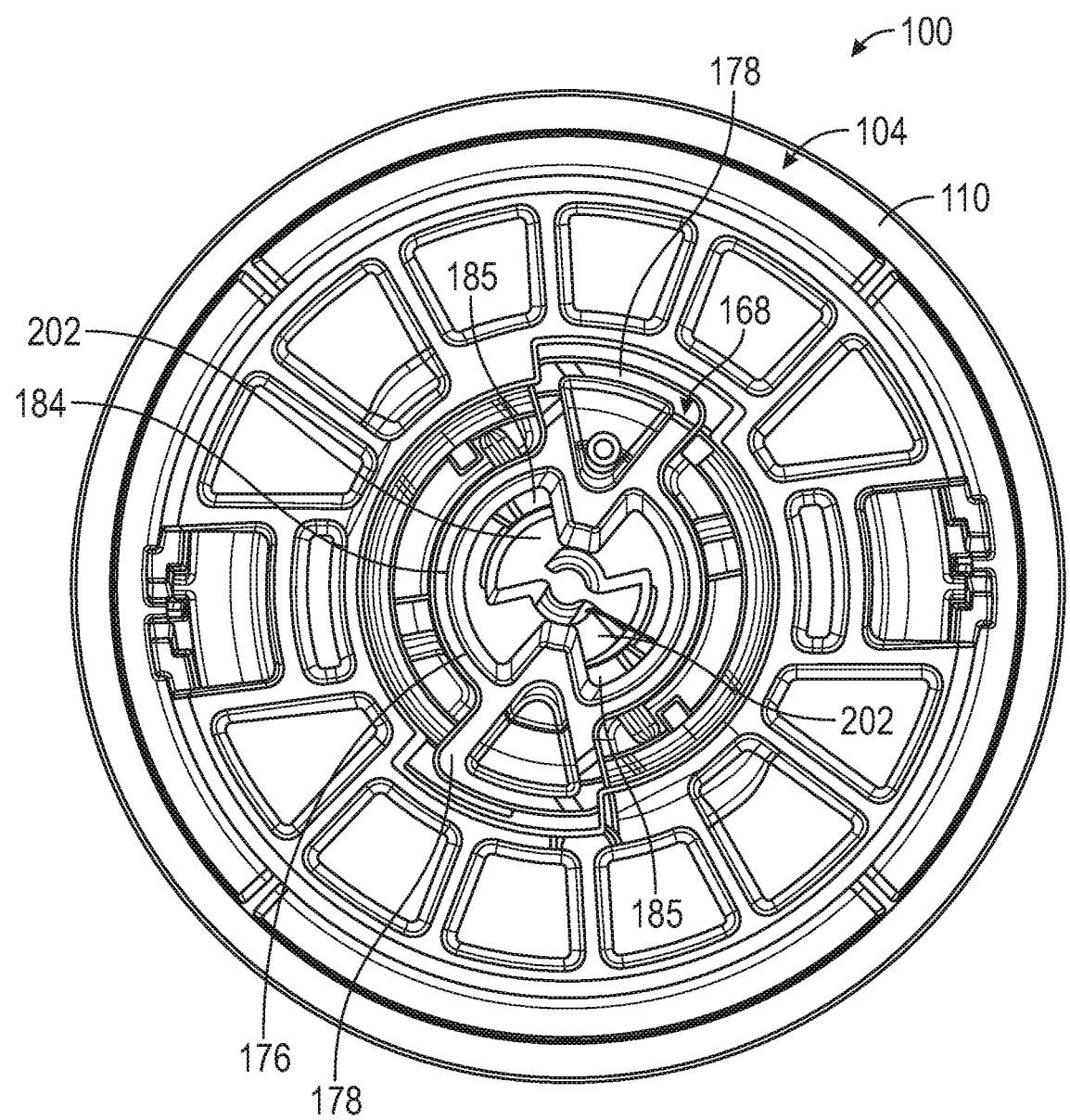
FIG. 26 is a second top plan view of the applicator of FIG. 25.

Referring to FIG. 15, when upper housing 104 is pushed down axially along axis X of applicator 100, firing spring 210 is compressed and, therefore, energized. Return spring 208 is also compressed, when this happens. Also, when upper housing 104 is pushed down axially along an axis X of applicator 100, latch 168 is rotationally displaced around axis X due to the interaction of latch 168 with an upper end of plunger post 194. Specifically, referring to FIGS. 21-26, the interaction of latch 168 and plunger 174 between an unprimed and primed state of applicator 100 is depicted. As upper housing 104 is pushed down axially, latch 168 is rotationally displaced in a clockwise direction around axis X due to the interaction of a ramped surface 187 on latch 168 with a ramped surface 203 on plunger 174. As plunger 174 continues to move up axially into bore 184 of latch 168, latch 168 continues to rotate in a clockwise direction until ramped surface 187 of latch 168 is able to slide past ramped surface 203 of tab 202, such that a counterclockwise torsional force of latch 168 created by latch spring 206, causes latch 168 to rotate backwards in a counterclockwise fashion until tab 202 on upper end 204 of plunger 174 can engage and couple with catch 185 in latch bore 184. FIG. 25 depicts a top plan view of applicator (with cap 113 removed) prior to priming, wherein tab 202 has not yet engaged with catch 185. FIG. 26 depicts a top plan view of applicator (with cap 113 removed) after priming, wherein tab 202 has engaged with catch 185.

Figure 16:
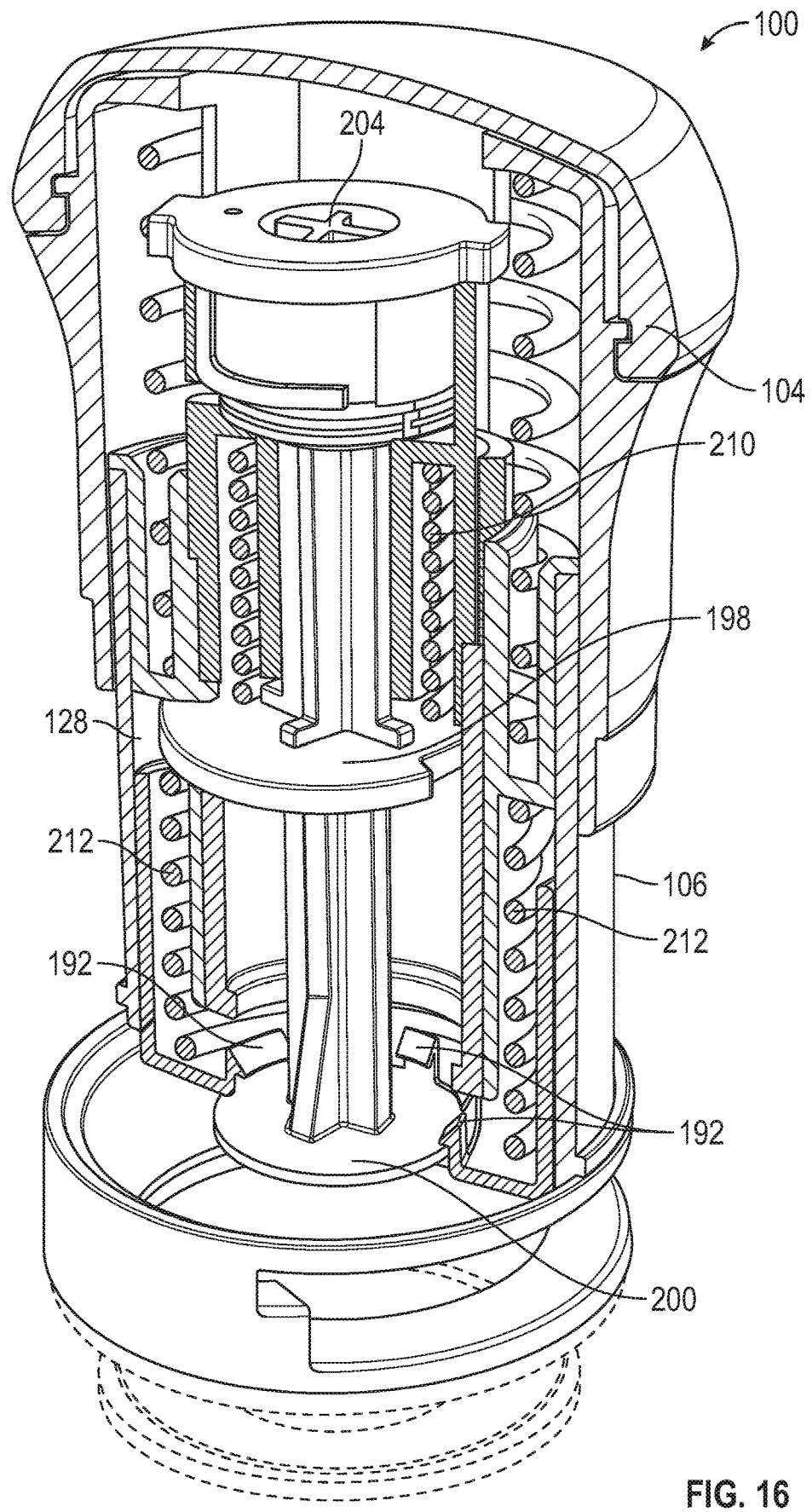
FIG. 16 is a top front perspective and partial cross-sectional view of the applicator of FIG. 14.
Figure 17:
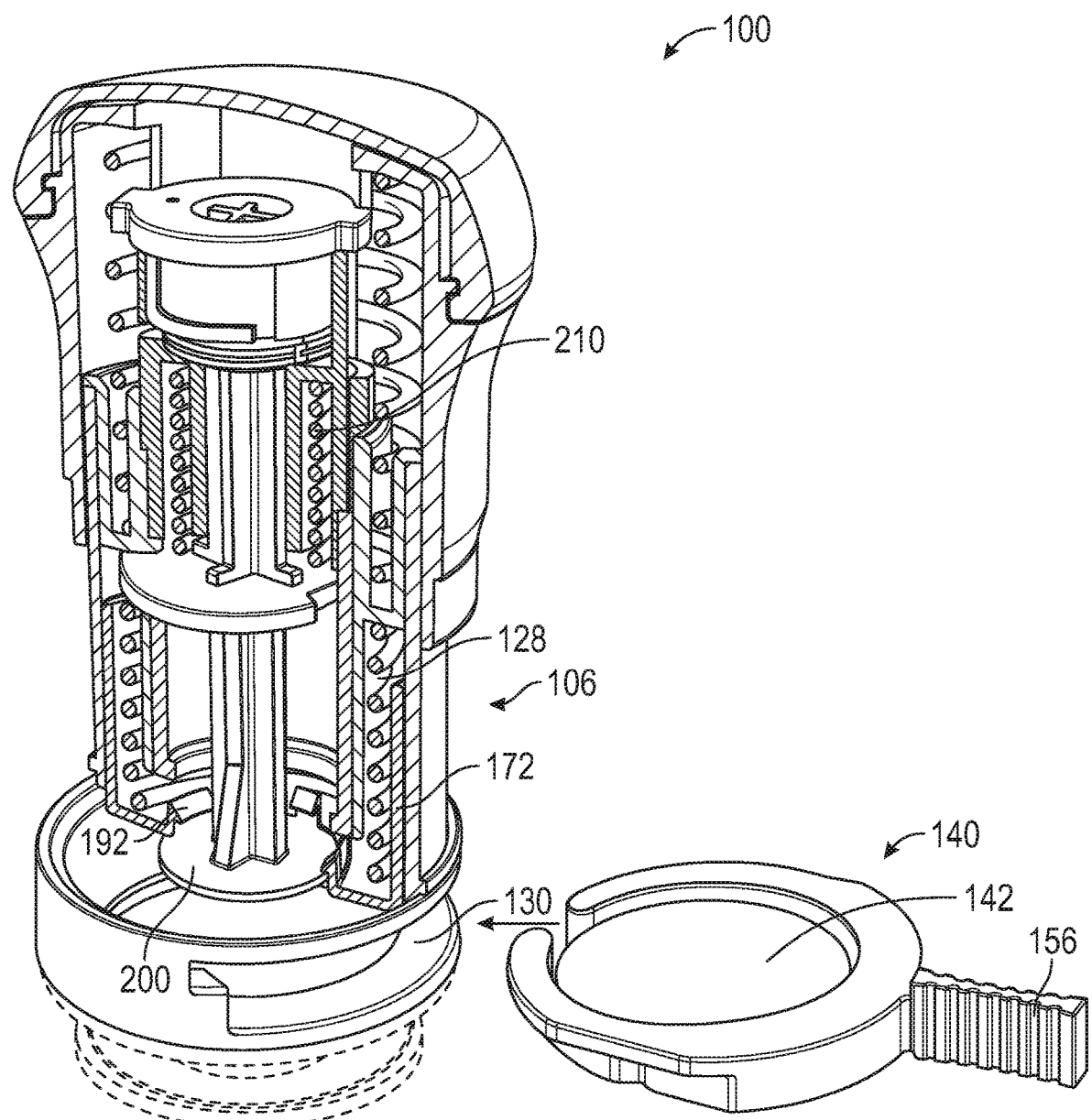
FIG. 17 is a top front perspective and partial cross-sectional view of the applicator of FIG. 14 and microneedle array carrier of FIG. 6.
Figure 18:
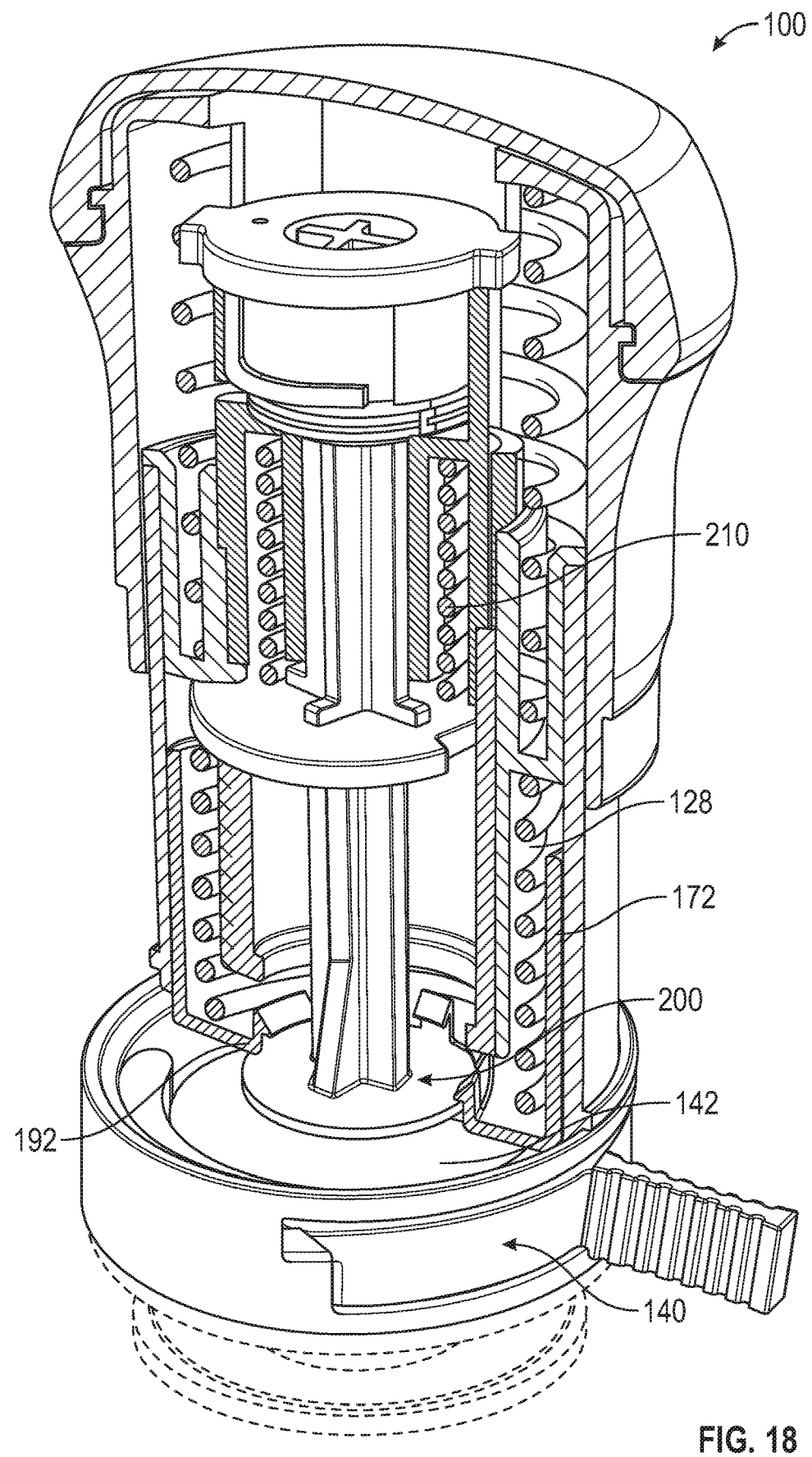
FIG. 18 is a top front perspective and partial cross-sectional view of the applicator of FIG. 14 and microneedle array carrier of FIG. 6.
Figure 19:
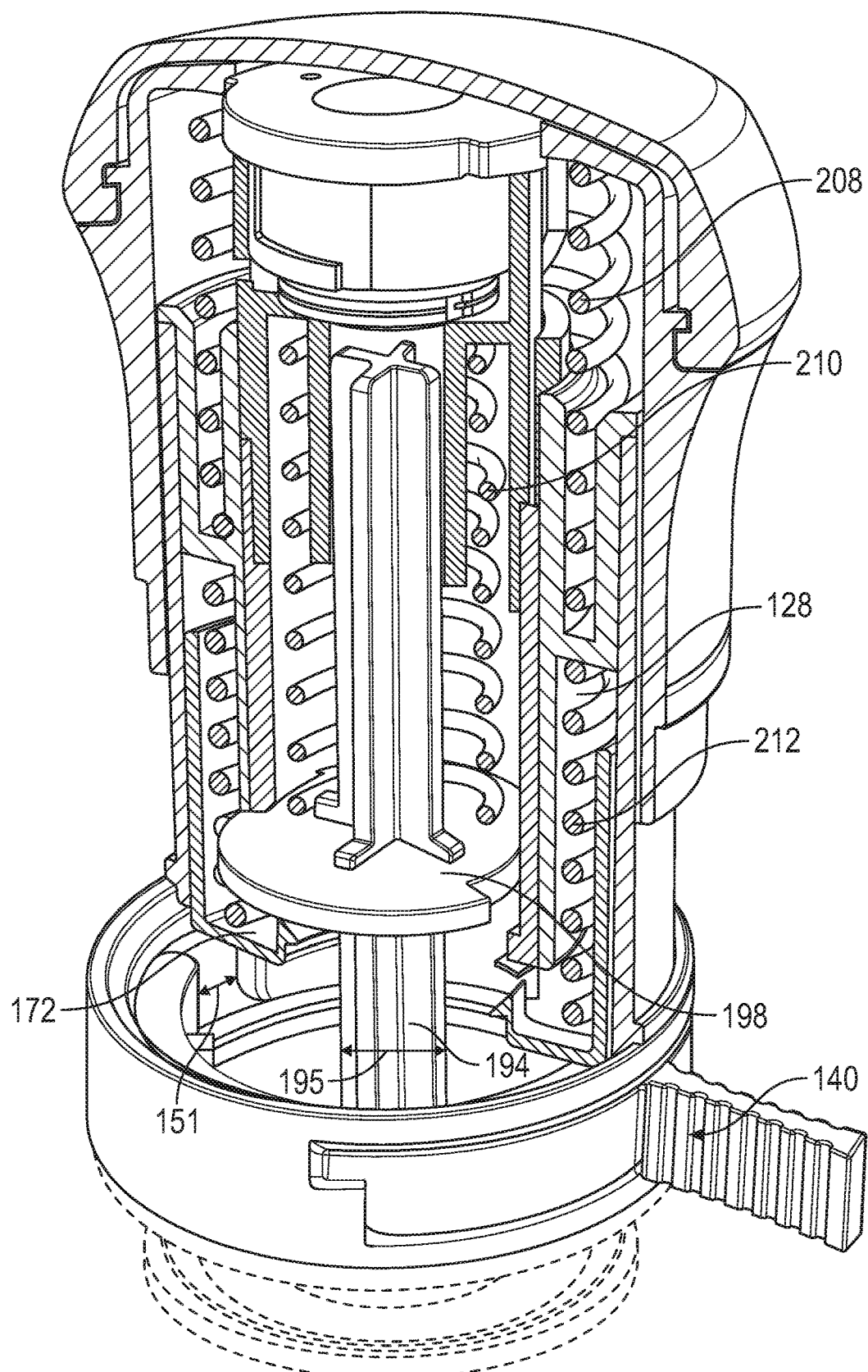
FIG. 19 is a top front perspective and partial cross-sectional view of the applicator of FIG. 14 and microneedle array carrier of FIG. 6.

After applicator 100 is primed, if a user releases compressional pressure from upper housing 104, applicator 100 returns to an extended position, as depicted in FIG. 16, due to return spring 208 returning to an uncompressed state. Insertion or firing spring 210 remains compressed or energized due to tab 202 and catch 185 being operably interlocked and plunger 174 is drawn up into upper housing 104. Because tabs 192 of door 172 engage and couple with second plunger disc 200 of plunger 174, when plunger 174 is drawn up, it brings door 172 with it. Referring to FIGS. 14 and 15, slot 130, where microneedle array carrier 140 can be inserted, is initially covered by door 172 at a bottom end of door 172. Door 172 (and bottom end) is drawn up when applicator 100 is in the position shown in FIG. 16, thus opening slot 130. This enables microneedle array carrier 140 to only be inserted into the slot 130 when applicator 100 has been primed and is ready to use. This also allows a patient to easily see if the applicator 100 has been primed or not by observing if the window is open or closed. Referring to FIGS. 17 and 18, once lower end of door 172 is removed from slot 130, microneedle array carrier 140 can be inserted into slot 130.

Referring to FIG. 17, once microneedle array carrier 140, with microneedle array assembly 142, has been inserted into slot 130, microneedle array assembly 142 can be applied to the skin by axially compressing, i.e., pushing down, on upper housing 104 again. That causes latch 168 to rotate in a clockwise fashion, which releases the spring-loaded plunger 174 by releasing tab 202 at upper end 204 of plunger 174—tab 202 and catch 185 operably slide on one another until no longer engaged and firing spring 210 releases to its uncompressed state. The second plunger disc 200 of spring-loaded plunger 174 can be positioned to rest directly against or very close to underside 167 of microneedle array assembly 142 once primed, or come into direct contact of come very close to bottom surface 167 of microneedle array assembly 142 when upper housing 104 is again pressed axially down, but before plunger 174 is released (i.e., applicator 100 is fired). By having this configuration, a user can inhibit instability issues that might arise if a plunger were to accelerate and hit a microneedle array assembly in order to release it from the carrier while still in the applicator. Instead, plunger 174 pushes microneedle array assembly 142 from microneedle array carrier 140 as it begins to accelerate and reaches the desired impact speed about a time, or substantially simultaneously with, the microneedle array assembly 142 contacting the skin.

Figure 27:
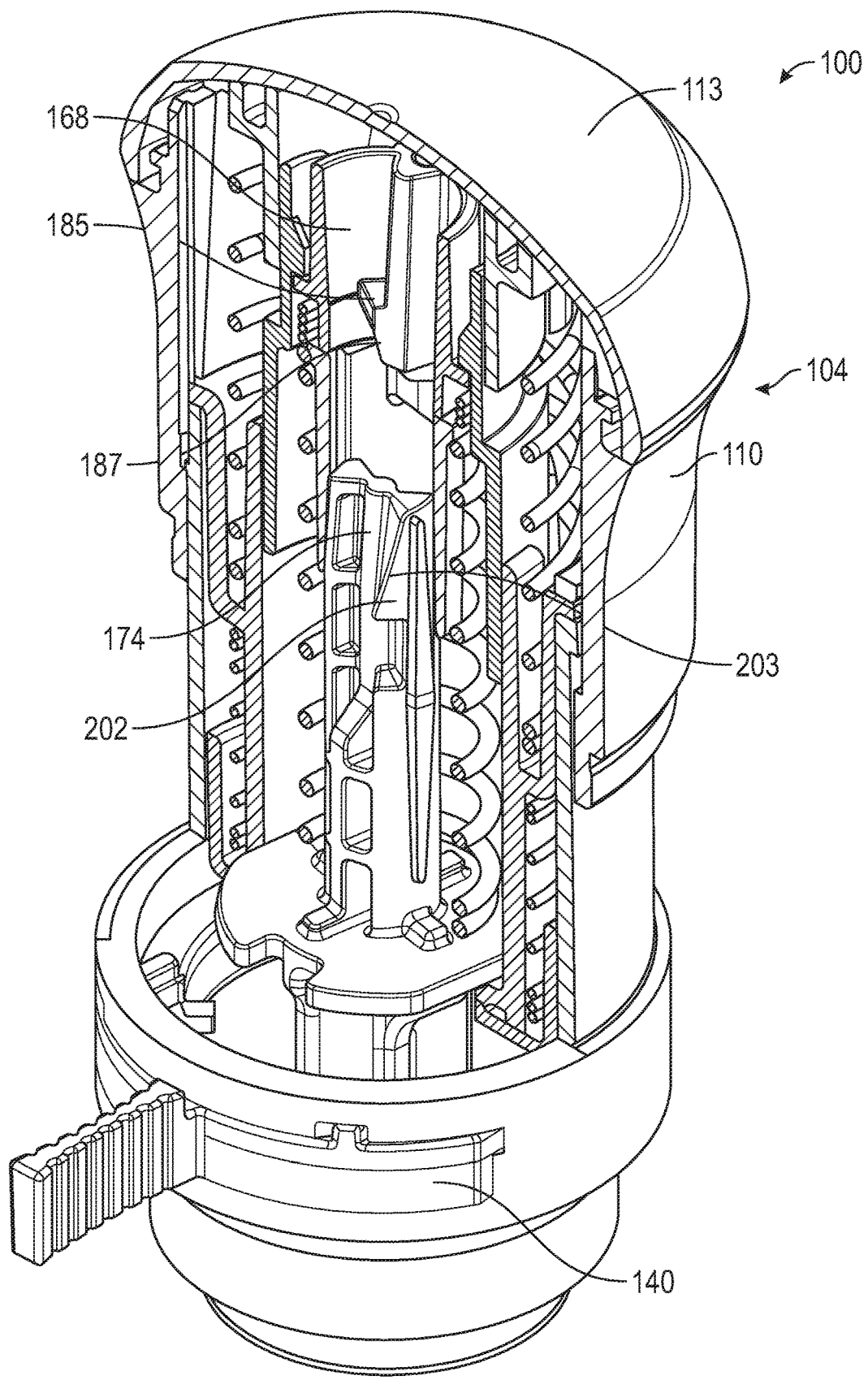
FIG. 27 is a first partial cut-away view of the applicator of FIG. 25 with the cap of upper housing in place.
Figure 28:
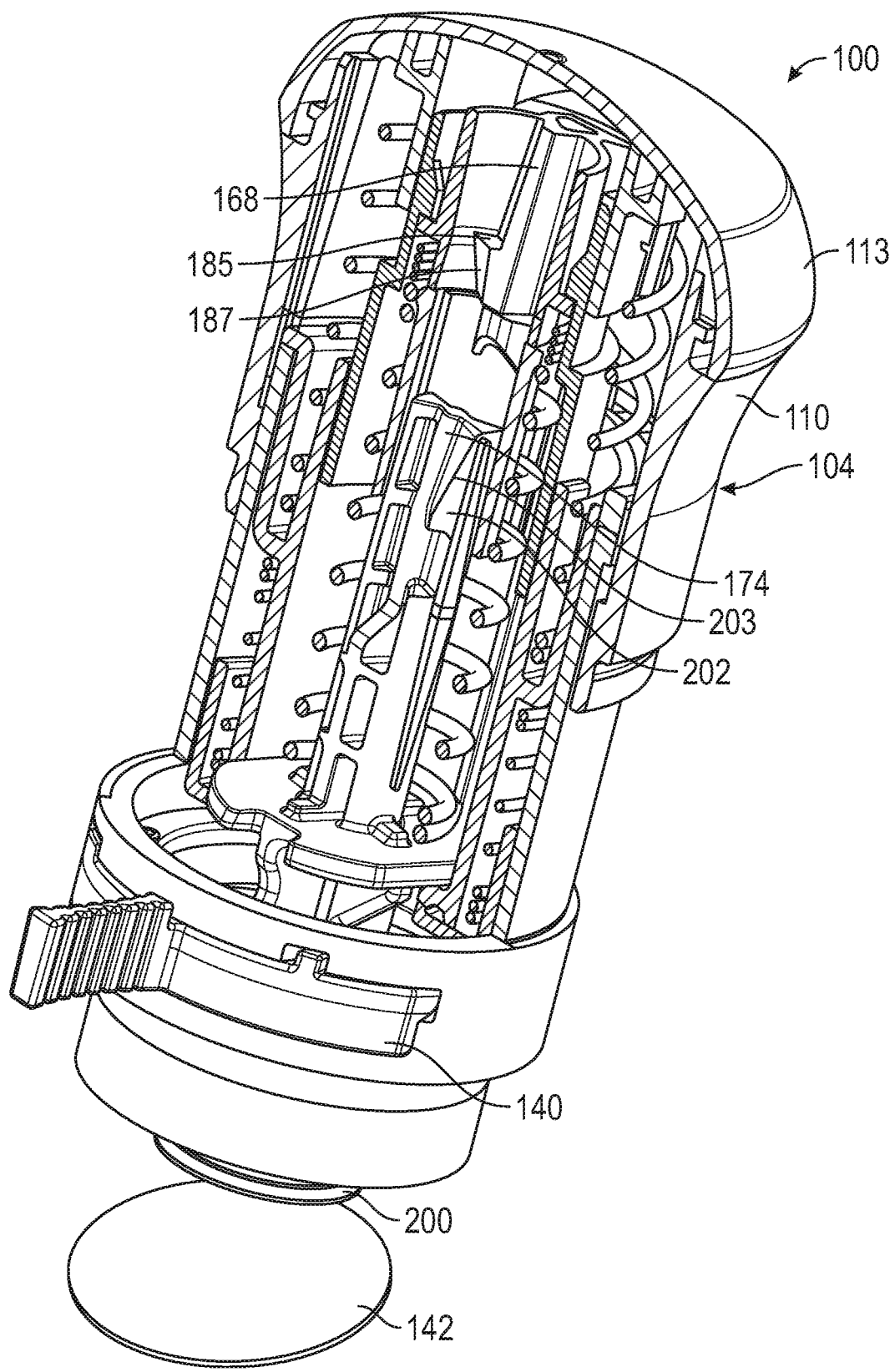
FIG. 28 is a second partial cut-away view of the applicator of FIG. 27.

FIGS. 27 and 28 depict catch 185 of latch and tab 202 of plunger 174 according to an embodiment after microneedle array assembly 142 has been applied to a surface, where, as described above, the shape of the plunger 174 and tabs 202 thereon comprise a different shape than that depicted in FIGS. 1-24. Those skilled in the art will recognize that further shapes and configurations of plungers 174 and tabs 202 can be used.

Figure 20:
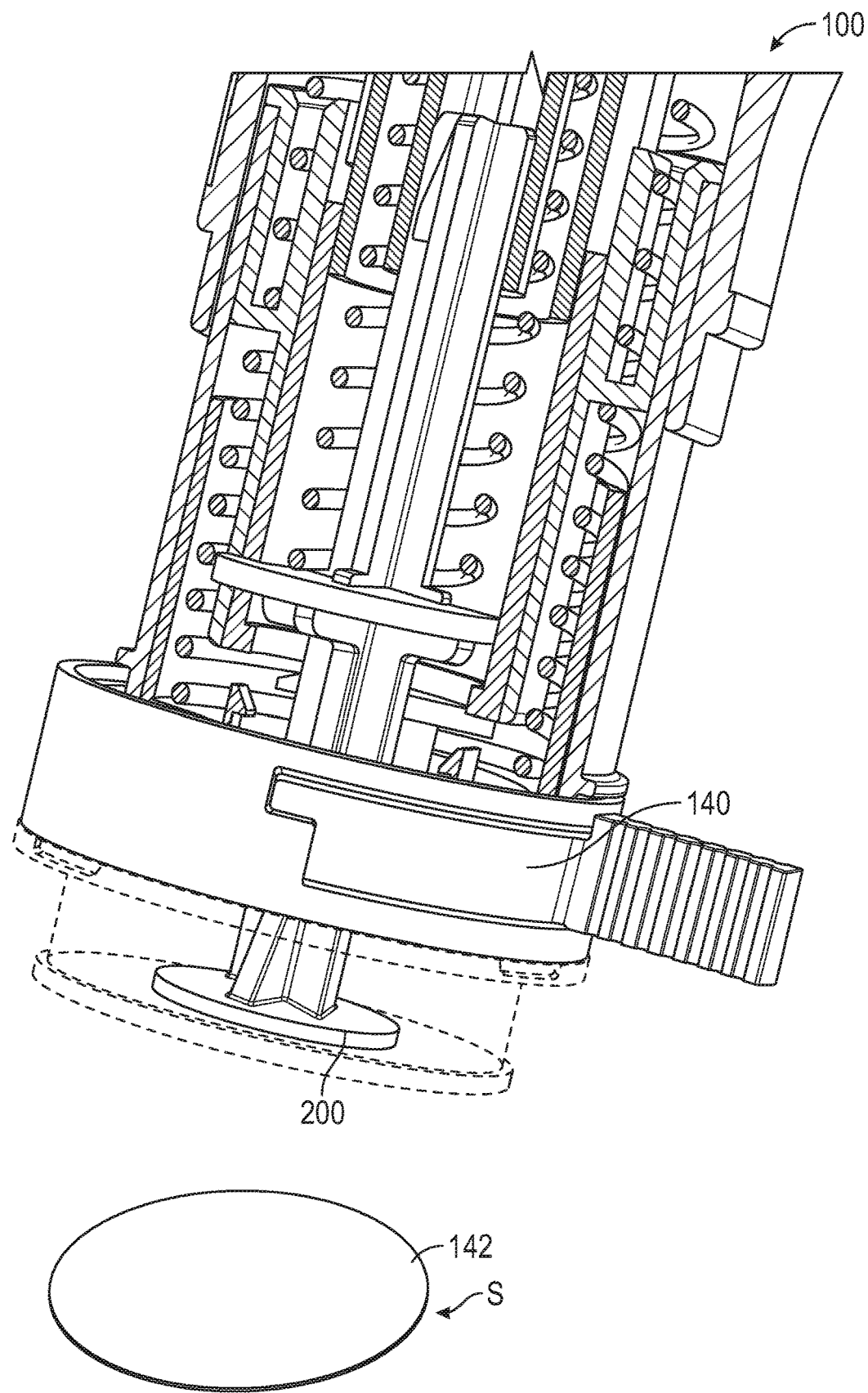
FIG. 20 is a top front perspective and partial cross-sectional view of the applicator of FIG. 14 and microneedle array carrier of FIG. 6.
Figure 21:
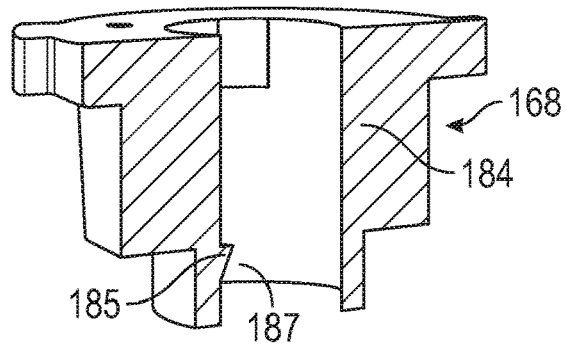
FIGS. 21-24 are close-up partial cross-sectional views of the applicator of FIG. 14 and microneedle array carrier of FIG. 6.
Figure 21:
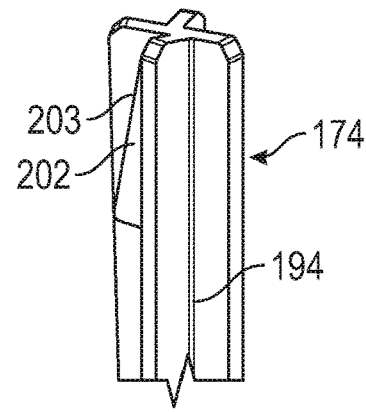
Figure 22:
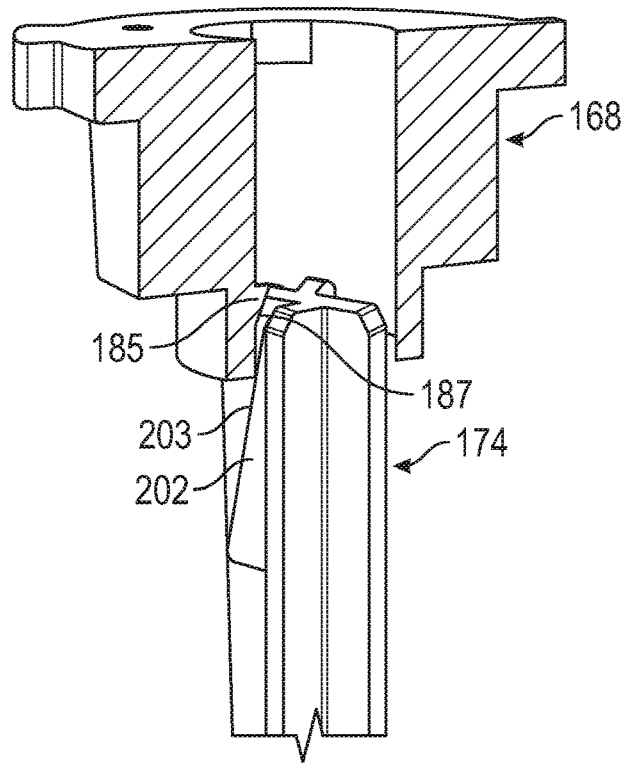
Figure 23:
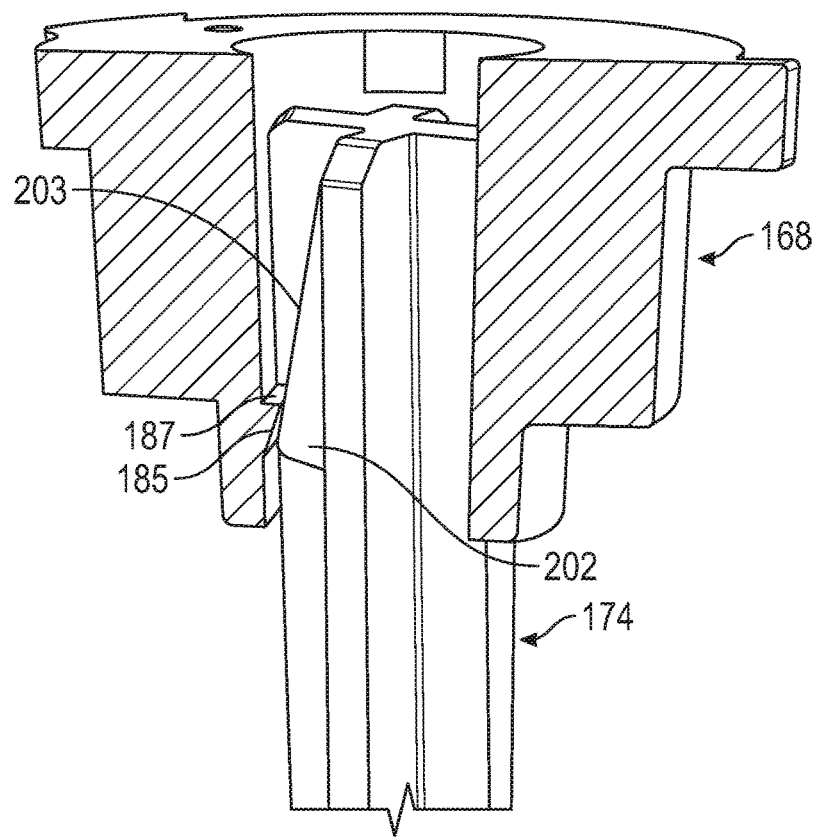
Figure 24:
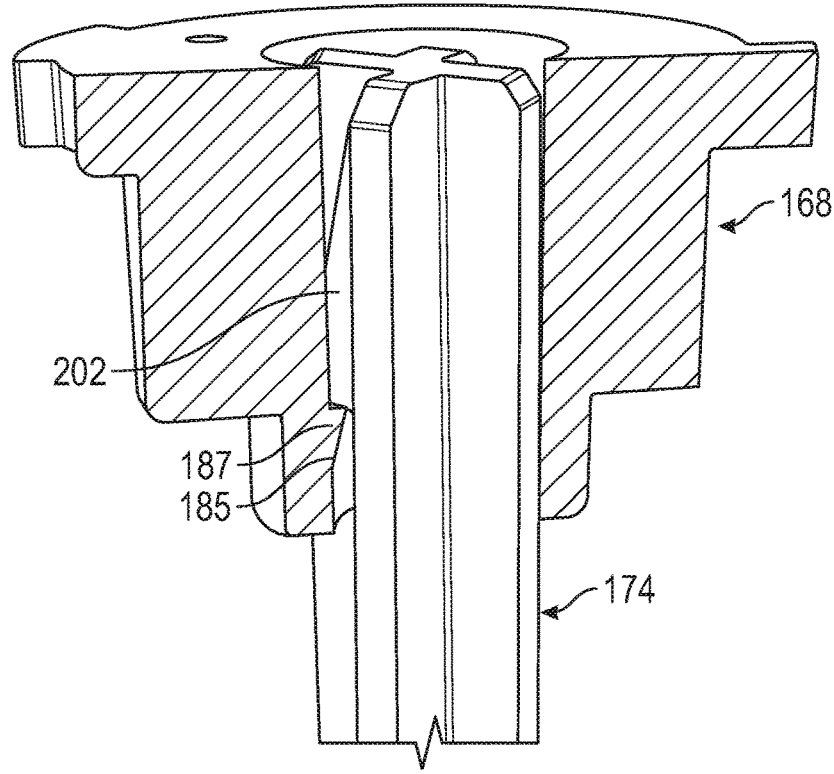

Referring to FIG. 20, in an embodiment, microneedle array assembly 142 is not affixed or held on second plunger disc 200 of plunger 174, so once it has been applied to a patient's skin there is no need to detach applicator 100 (i.e., second plunger disc 200 of plunger 174) from microneedle array assembly 142. Microneedle array assembly 142 is affixed to the skin and applicator 100 can be removed without disturbing microneedle array assembly 142

After microneedle array assembly 142 has been delivered and affixed to a patient, microneedle array carrier 140 can be removed from slot 130 returning applicator to its original orientation. Due to its shape, for example, its "C" shape, an open end on microneedle array carrier 140 generally opposed handle 156 enables microneedle array carrier 140 to be removed from slot 130 in applicator 100 despite plunger 174, including plunger post 194, being in its extended position.

The complete disclosures of the patents, patent documents and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A device for applying a microneedle array to a surface, said device comprising:
   a body comprising a first portion and a second portion defining a cavity, said second portion comprising a slot presented on an outside surface of said second portion for insertion of the microneedle array into said cavity, said first portion and said second portion slidable relative to one other along an axis thus enabling said device to be in an unprimed configuration and a primed configuration; and
   a plunger disposed in said cavity, said plunger comprising a first plunger end and a second plunger end, said plunger movable from a first position when said device is in said unprimed configuration to a second position when said device is in said primed configuration, and a microneedle array;
   wherein when said device is in said primed configuration, the microneedle array is adapted to be inserted into said cavity through said slot and positioned proximate said second plunger end, and further wherein the plunger is adapted to contact the microneedle array when the device is in the primed configuration and the first portion and the second portion of the body are axially compressed but before the plunger is released.

2. The device of claim 1, wherein after the microneedle array is inserted in said slot and positioned proximate said second plunger end, the microneedle array and said second plunger end are in contact with one another when the plunger is in the second position but before the first and second portions of the body are axially compressed.

3. The device of claim 1, wherein after the microneedle array is inserted in said slot and positioned proximate said second plunger end, the microneedle array and said second plunger end are less than about 2 mm from one another when the plunger is in the second position but before the first and second portions of the body are axially compressed.

4. The device of claim 1, wherein after the microneedle array is inserted in said slot and positioned proximate said second plunger end, the microneedle array and said second plunger end are less than about 1 mm from one when the plunger is in the second position but before the first and second portions of the body are axially compressed.

5. The device of claim 1, wherein after the microneedle array is inserted in said slot and positioned proximate said second plunger end, the microneedle array and said second plunger end are less than about 0.5 mm from one another when the plunger is in the second position but before the first and second portions of the body are axially compressed.

6. The device of claim 1, wherein said second portion comprises an inner surface comprising a low surface energy material, wherein when said plunger moves from said first position to said second position, any friction between the microneedle array and said inner surface, should they be in slidable engagement with one another, is minimized.

7. The device of claim 1, further comprising a biasing member for biasing said plunger to said first position when said device is in said unprimed configuration.

8. The device of claim 7, wherein said biasing member comprises a compression spring and wherein said compression spring is compressed and energized when said plunger is in said second position when said device is in said primed configuration.

9. The device of claim 1, further comprising visual indicia proximate the slot identifying a location of the slot to a user.

* * * * *